United States Patent
Cegla et al.

(10) Patent No.: US 10,537,916 B2
(45) Date of Patent: Jan. 21, 2020

(54) ELECTROMAGNETIC ACOUSTIC TRANSDUCER

(71) Applicant: PERMASENSE LIMITED, Worthing West Sussex (GB)

(72) Inventors: Frederic Bert Cegla, Horsham (GB); Julio Agustin Isla Garcia, Horsham (GB)

(73) Assignee: PERMASENSE LIMITED, Worthington West Sussex (GB)

( * ) Notice: Subject to any disclaimer, the term of this patent is extended or adjusted under 35 U.S.C. 154(b) by 111 days.

(21) Appl. No.: 15/522,481

(22) PCT Filed: Oct. 22, 2015

(86) PCT No.: PCT/GB2015/053161
§ 371 (c)(1),
(2) Date: Apr. 27, 2017

(87) PCT Pub. No.: WO2016/066997
PCT Pub. Date: May 6, 2016

(65) Prior Publication Data
US 2017/0333946 A1    Nov. 23, 2017

(30) Foreign Application Priority Data

Oct. 29, 2014    (GB) .................................. 1419219.9

(51) Int. Cl.
*B06B 1/04*    (2006.01)
*B06B 1/08*    (2006.01)
*G01N 29/24*    (2006.01)

(52) U.S. Cl.
CPC .............. *B06B 1/04* (2013.01); *B06B 1/08* (2013.01); *G01N 29/2412* (2013.01); *G01N 2291/0422* (2013.01)

(58) Field of Classification Search
CPC ........ B06B 1/04; B06B 1/08; G01N 29/2412; G01N 29/024; G01N 29/032; G01N 29/04
See application file for complete search history.

(56) References Cited

U.S. PATENT DOCUMENTS

| | | | | |
|---|---|---|---|---|
| 4,348,903 A | * | 9/1982 | Sato | .................... G01N 29/2412 73/643 |
| 4,450,725 A | * | 5/1984 | Yamaguchi | ............ G01B 17/02 505/879 |

(Continued)

FOREIGN PATENT DOCUMENTS

| CN | 86106267 | 5/1987 |
|---|---|---|
| CN | 2816822 | 9/2006 |

(Continued)

OTHER PUBLICATIONS

Website: http://www.nordinkraft.de/EMATEST-PL.pdf, XP055242834, Dated Apr. 28, 2014, 8 Pages, "Equipment for automatic ultrasonic testing plates EMATEST-PL".

(Continued)

*Primary Examiner* — Helen C Kwok
(74) *Attorney, Agent, or Firm* — Brooks Kushman P.C.

(57) ABSTRACT

An electromagnetic acoustic transducer includes a flux guide surrounded by one or more permanent magnets abutting side faces of the flux guide. The magnetic field from the permanent magnets enters the flux guide where repulsion between the magnetic fields directs at least a portion of the magnetic fields toward a test face abutting a test object. The flux density at the test face is greater than the flux density within the originating permanent magnets. An active portion of a coil disposed between the flux guide and the test object contains conductors that are substantially straight, parallel and carry current in the same direction in order to provide substantially mode pure and uni-directionally polarised excitation of shear waves within the test object.

16 Claims, 19 Drawing Sheets

(56) References Cited

U.S. PATENT DOCUMENTS

| | | | | |
|---|---|---|---|---|
| 4,471,658 | A | * | 9/1984 | Morimoto ................ B06B 1/04 |
| | | | | 324/220 |
| 4,481,824 | A | * | 11/1984 | Fujimoto ............... G01N 29/11 |
| | | | | 73/599 |
| 4,523,473 | A | * | 6/1985 | Chamuel ............. G01N 27/725 |
| | | | | 73/583 |
| 4,596,147 | A | * | 6/1986 | Behl .................. G01N 29/2412 |
| | | | | 73/643 |
| 4,638,830 | A | | 1/1987 | Brown et al. |
| 4,689,996 | A | * | 9/1987 | Huschelrath ....... G01N 29/2412 |
| | | | | 73/598 |
| 5,148,414 | A | * | 9/1992 | Graff ........................ B06B 1/04 |
| | | | | 367/140 |
| 5,608,691 | A | * | 3/1997 | MacLauchlan ........... B06B 1/04 |
| | | | | 367/140 |
| 5,837,898 | A | * | 11/1998 | MacLauchlan ....... G01F 23/284 |
| | | | | 73/599 |
| 2007/0074572 | A1 | * | 4/2007 | Koch ........................ B06B 1/04 |
| | | | | 73/627 |
| 2009/0139335 | A1 | * | 6/2009 | Kroning .................... B06B 1/04 |
| | | | | 73/597 |

FOREIGN PATENT DOCUMENTS

| | | | |
|---|---|---|---|
| DE | 4011686 | * | 7/1991 |
| EP | 0451375 | | 10/1991 |
| GB | 1349726 | * | 4/1974 |
| JP | S5286388 | | 7/1977 |
| JP | S5621058 | | 2/1981 |
| JP | S5995453 | | 6/1984 |
| JP | S6175259 | | 4/1986 |
| JP | 6256857 | * | 3/1987 |
| JP | S62-56857 | A | 3/1987 |
| JP | S62277555 | | 12/1987 |
| JP | H09281088 | | 10/1997 |
| JP | 2007527532 | | 9/2007 |
| JP | 2009503497 | | 1/2009 |
| WO | 2007013836 | | 2/2007 |

OTHER PUBLICATIONS

Search Report for Application No. GB 1507388.5, Completed by the United Kingdom Intellectual Property Office dated Sep. 7, 2015, 5 Pages.

Search Report for Application No. GB 1507388.5, Completed by the United Kingdom Intellectual Property Office dated Oct. 1, 2015, 3 Pages.

Search Report for Application No. GB 1419219.9, Completed by the United Kingdom Intellectual Property Office dated Feb. 10, 2015, 5 Pages.

International Search Report for PCT/GB2015/053161, Completed by the European Patent Office dated Jan. 25, 2016, 4 Pages.

Written Opinion for PCT/GB2015/053161, Completed by the European Patent Office, dated Sep. 21, 2016, 7 Pages.

Japanese Office Action for Japanese Application No. JP2017-542352, English Translation attached to original, dated Jun. 5, 2018, All together 9 Pages.

Chinese Office Action for Application No. CN201580059321.1, dated Oct. 19, 2018, 10 Pages.

Eurasian Office Action for Application No. 201790815/31, English Translation attached to original, dated Oct. 12, 2018, All together 3 Pages.

Youtube Link: https://www.youtube.com/watch?v=jqg2RIJcgm8, Uploaded on Aug. 8, 2013, Accessed on Nov. 14, 2018, 2 Minutes and 15 seconds, "Ultrakraft. Электромагнитный акустический преобразователь (EMAT)", English Translation of Title "Ultrakraft. Electromagnetic Acoustic Transducer (EMAT)".

Japanese Office Action for Application No. 2017-542352, dated Feb. 5, 2019, 2 Pages.

EP Office Action for Application No. 15 790 191.9-1020, dated Nov. 11, 2018, 3 Pages.

* cited by examiner

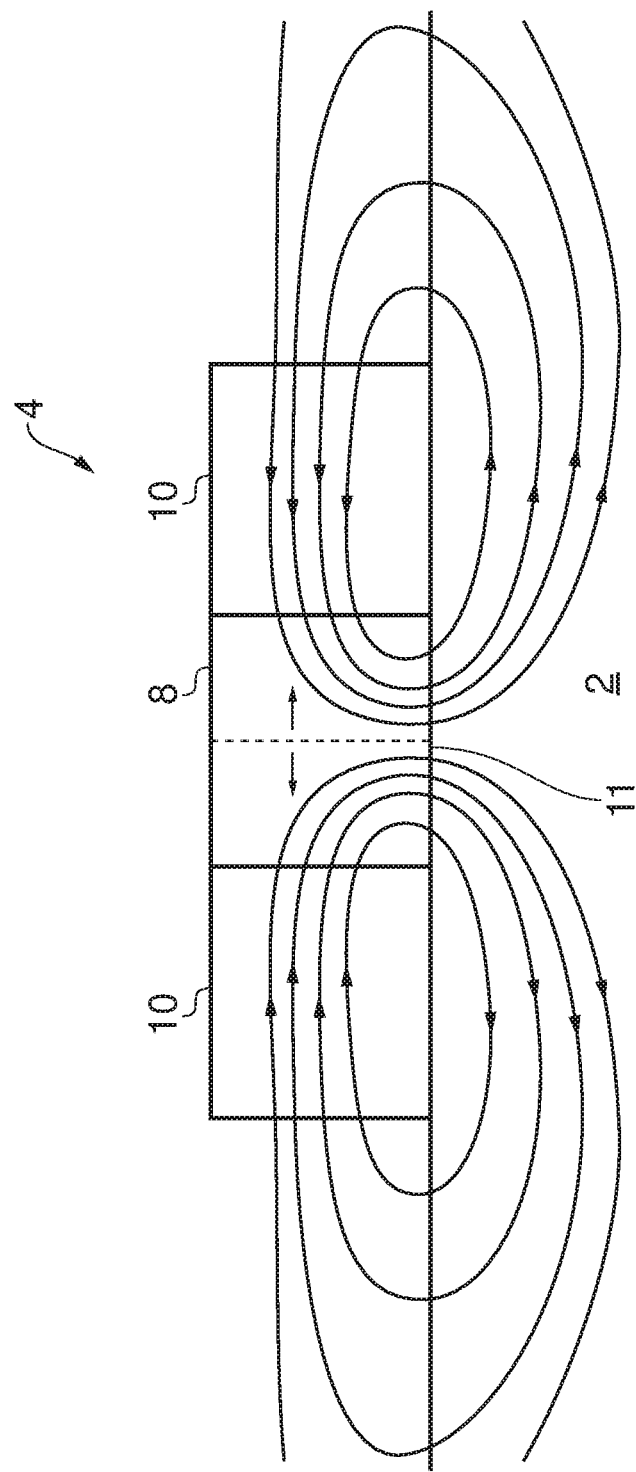

Fluxguide Cross Sections

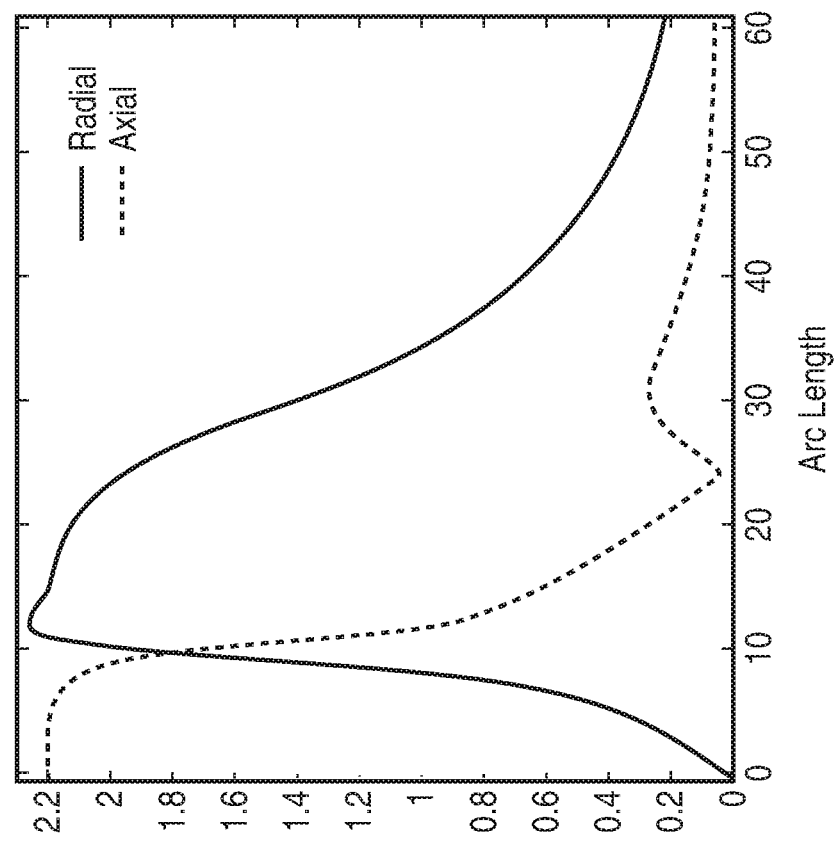
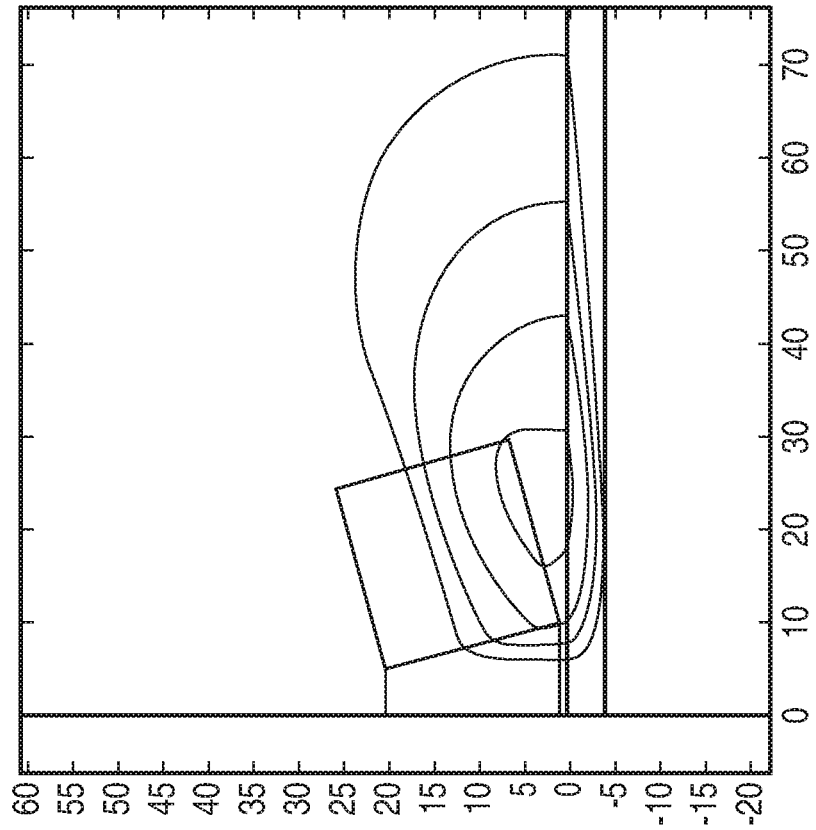
FIG. 11

ELECTROMAGNETIC ACOUSTIC TRANSDUCER

CROSS-REFERENCE TO RELATED APPLICATION

This application is the U.S. national phase of PCT Application No. PCT/GB2015/053161 filed on Oct. 22, 2015, which claims priority to GB Patent Application No. 1419219.9 filed on Oct. 29, 2014, and GB Patent Application No. 1507388.5 filed on Apr. 30, 2015 the disclosures of which are incorporated in their entirety by reference herein.

This disclosure relates to the field of electromagnetic acoustic transducers.

Conventional ultrasonic testing requires the use of coupling fluid between the transducer and the test structure. Electromagnetic acoustic transducers (EMATs) are attractive as they do not require coupling fluids, or even direct contact, between the transducer and the test object. Such characteristics are advantageous when, for example, monitoring for corrosion when sensing through corrosion protection layers (such as paint) is required. However, these advantages of EMATs are accompanied by the disadvantage that EMATs typically have a low sensitivity. To address this low sensitivity, one approach is to use high power excitation signals and high excitation voltages within the EMATS. However, this approach may not be possible for safety reasons in some installations.

Viewed from one aspect the present disclosure provides an electromagnetic acoustic transducer for exciting ultrasonic vibrations within a test object, said electromagnetic acoustic transducer comprising:

at least one magnet configured to generate a magnetic field;

a fluxguide having a test face for placing against said test object, said fluxguide shaped to receive said magnetic field from said at least one magnet and to direct said magnetic field such that repulsion between magnetic field lines within said fluxguide directs at least part of said magnetic field towards said test face; and an electrical coil, at least an active portion of said electrical coil disposed to cover said test face, wherein within said active portion conductors of said electrical coil are substantially parallel, straight and carrying current in a same direction.

The present disclosure recognises that the sensitivity of the electromagnetic acoustic transducer can be improved if the flux density at the test face is increased in some embodiments the flux density at the test face may be more than double the flux density with the magnet(s). Conventional permanent magnets are limited in the flux density that they can individually generate. The present disclosure recognises that using an appropriately shaped fluxguide receiving the magnetic field from the one or more magnets can result in an amplification of the flux density at the test face due to repulsion between magnetic field lines directing the magnetic field towards the test face.

Excitation of the acoustic waves by the transducer is achieved using an electrical coil with at least part of this electrical coil disposed over the test face. Within the active portion of the coil between the test face and the test object conductor of the electrical coil are substantially parallel, straight and carrying current in a same direction. This may produce ultrasonic waves of single polarity (e.g. shear waves polarised in one direction). This improves mode purity. Improved mode purity (e.g. a single mode excited) may make processing and interpretation of returned signals more straightforward (e.g. avoids ambiguity and a reduction in resolution due to received overlapping signals corresponding to different modes (e.g. longitudinal and shear wave modes) received at the same time).

Example embodiments which have been found to provide good performance (e.g. sensitivity) are those in which the electrical coil is a butterfly coil comprising two adjacent spiral coils wound in opposite directions. Such a butterfly coil may be conveniently located between the flux guide and the test object such that a medial portion of the butterfly coil between the adjacent spiral coils is disposed directly between the test face and the test object. This may permit generation of ultrasound waves with a high mode purity.

The dimensions of the fluxguide relative to the magnet(s) are important to provide a strong magnetic field with a compact transducer. The test face has dimensions such that a smallest radius of a circle wholly containing a projection of the test face into a plane normal to a mean direction of magnetic flux lines passing through the test face is $R_a$. The magnet(s) have dimensions such that a smallest radius of a circle wholly containing a project of the magnet(s) in the plane is $R_b$ and $R_a/R_b$ is in the range 0.2 to 0.8, or is some embodiments in the range 0.45 to 0.55.

The value of $R_a$ may conveniently be in the range 2.5 mm to 25 mm or in the same embodiments 5 mm to 10 mm.

The height H of the fluxguide normal to the plane may be in the range 0.2 to $10R_a$. Good performance with a compact size may be achieved when H is in the range $R_a$ to $4R_a$ or in the range 5 mm to 50 mm.

There are a wide variety of different possible geometries for the at least one magnet and the fluxguide. A desirable degree of amplification in the magnetic flux density at the test face may be achieved in some example embodiments in which the at least one magnet has one or more magnet faces proximal to the fluxguide and the magnetic field passes between the one or more magnet faces and the fluxguide in respective directions that are non-normal to the test face. Such an arrangement facilitates concentration of the magnetic field around the test face.

In some example embodiments, the directions of the normal to the magnet faces may be within a range of 90 degrees to 15 degrees from a normal to the test face. Such a range of angles provides a geometry yielding a useful amplification in the magnetic flux density. In other example embodiments in which the amplification is greater, the directions at which the magnetic field passes from the magnets to the fluxguide may be within a range of 90 degrees to 30 degrees from a normal to the test face. Further example embodiments in which an advantageous amplification in the flux density balanced against a compact form are particularly strong are those in which the directions at which the magnetic field lines enter the fluxguide are substantially perpendicular to a normal to the test face.

It will be appreciated that the fluxguide can have a variety of different forms. It would be possible for the fluxguide to have the shape of a cylinder with the magnet being a single magnet formed as an annulus surrounding this cylinder. In other embodiments, the fluxguide has the shape of a prism or frustum and the test face is a polygonal base face of this prism or frustum. The fluxguide is not limited to the shape of a right prism, also oblique prisms, pyramids and frustra are possible; examples range from right and oblique triangular prisms, via square or polygonal pyramids to polygonal frustra in the limit approaching a capped cone. The base face of the fluxguide may in some embodiment have N edges, where N is in the range 4 to 8.

With such an arrangement, the at least one magnet may be conveniently provided as a plurality of magnets with respective pole faces and the prism or frustum provided with a plurality of side faces that join the test face with at least some of the pole faces of the magnets abutting at least some of the side faces of the prism or frustum. The same polarity of pole of the magnets may abut all of the side faces of the prism or frustum.

An increased flux density at the test face may be achieved when each of the plurality of side faces is abutted by one of the pole faces. The geometry and forming of the transducer so as to give a regular field may be improved when the prism is a right prism.

While it will be appreciated that the polygonal face could have the form of a wide variety of different regular or irregular polygons, some example embodiments which provide a good balance between performance and complexity are ones in which the test face is a quadrilateral and the prism is a cuboid. Symmetry and regularity may be improved when the test face is a square.

A convenient packaging of the overall transducer enabling simplified deployment and fixing of the transducer may be achieved in example embodiments in which a total area occupied by the electrical coil is contained within a total cross-sectional area occupied by the electromagnetic acoustic transducer projected normally onto the test object. In this way, the coil does not project beyond the transducer and may be protected and held within the transducer body itself.

The robustness against noise and/or performance of the transducer may be improved in some example embodiments by providing a capacitive shield disposed between the electrical coil and the test object. Such a capacitive shield may serve at least partially to block an electric field and to pass substantially all of a dynamic magnetic field from the coil on transmission and from the eddy currents upon reception. In this way, the desired magnetic field may be passed and used to excite desired ultrasonic vibrations and desired voltages in the coil, whereas an electric field which may introduce noise into the system is attenuated.

The capacitive shield may be formed as a conductive plate having one or more cuts therein with those cuts positioned so as to reduce induction of eddy currents in the conductive plate by the electrical coil. The form of the electrical coil will control the direction of any induced eddy currents and the cuts can be positioned relative to the electrical coil so as to inhibit the generation of eddy currents in the conductive plate.

The capacitive shield may also serve, in some example embodiments, as a wear plate serving to protect the electrical coil in what may be a harsh deployment environment.

The electromagnetic acoustic transducer of at least some example embodiments may be held to the test object by one or more of magnetic attraction between the fluxguide/magnet(s) and the test object, a resilient clamping structure accommodating attachment to a non-planar test object, and a clamp encircling a test object that is a pipe. In practice, the strong magnetic attraction between an electromagnetic acoustic transducer in accordance with the present techniques and a suitable test object significantly simplifies fixing the transducer to the test object and helps to resist lift off whereby displacement of the transducer, such that the test face is no longer in close contact with the test object, may be resisted.

A housing surrounding the fluxguide and the magnet(s) may be "transparent" to the magnetic flux, e.g. have a magnetic permeability less than $2\mu_o$, where $\mu_o$ is the permeability of free space.

Viewed from another aspect the present disclosure provides an electromagnetic acoustic transducer for exciting ultrasonic vibrations within a test object, said electromagnetic acoustic transducer comprising:

at least one magnet configured to generate a magnetic field; and a fluxguide having a test face for placing against said test object, said fluxguide shaped to receive said magnetic field from said at least one magnet and to direct said magnetic field such that repulsion between magnetic field lines within said fluxguide directs at least part of said magnetic field towards said test face; wherein said test face has dimensions such that a smallest radius of a circle wholly containing a projection of said test face in a plane normal to a mean direction of magnetic field lines passing through said test face is Ra;

said at least one magnet has dimensions such that a smallest radius of a circle wholly containing a projection of said at least one magnet in said plane is Rb; and Ra/Rb is in the range 0.2 to 0.8.

Viewed from a further aspect the present disclosure provides a method of exciting ultrasonic vibrations within a test object using an electromagnetic acoustic transducer, said method comprising the steps of:

placing a fluxguide with a test face against said test object;

generating a magnetic field with at least one magnet;

receiving in said fluxguide said magnetic field from said at least one magnet; and directing said magnetic field within said fluxguide such that repulsion between magnetic field lines directs at least part of said magnetic field towards said test face;

disposing at least an active portion of an electrical coil disposed to cover said test face, wherein within said active portion conductors of said electrical coil are substantially parallel, straight and carrying current in a same direction.

Example embodiments of the present disclosure will now be described, by way of example only, with reference to the accompanying drawings in which:

FIG. 1 schematically illustrates an electromagnetic acoustic transducer fixed to a test object in the form of a pipe within a system for performing remote monitoring of that pipe (e.g. corrosion monitoring and/or defect detection);

Figure 2:
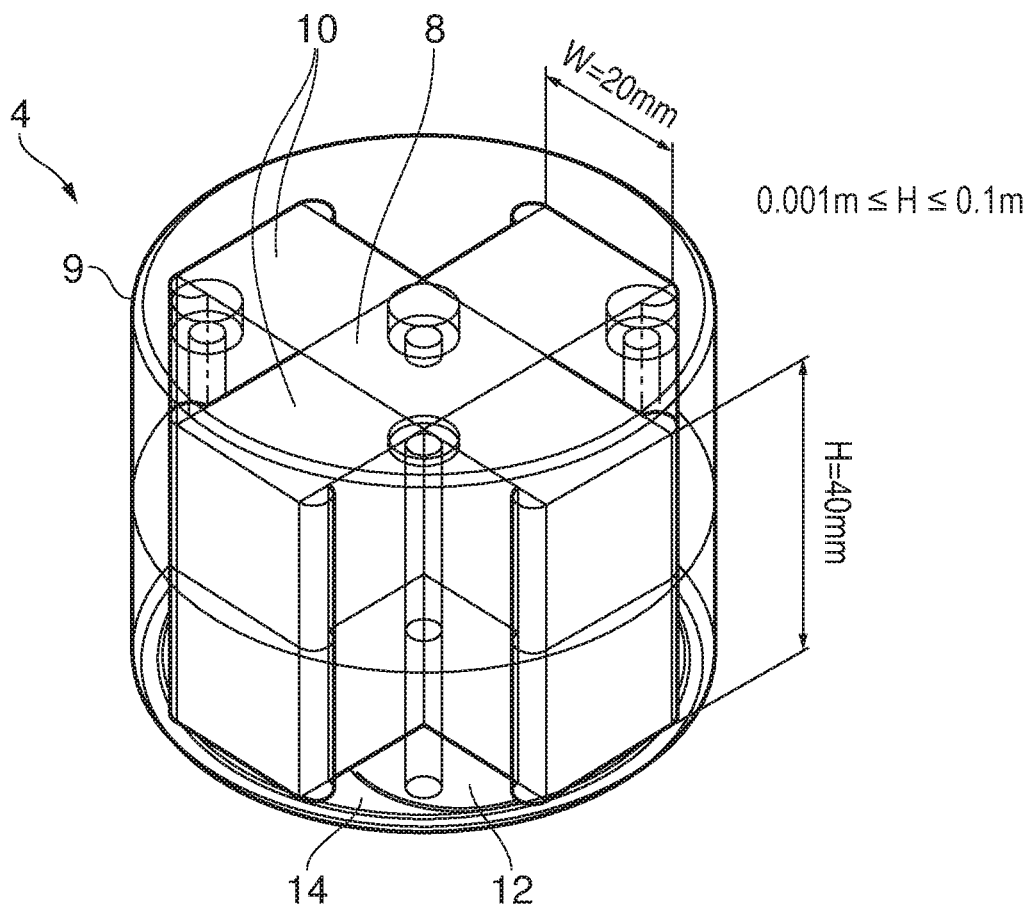
FIG. 2 is a diagram schematically illustrating a partially transparent perspective view of an electromagnetic acoustic transducer.
Figure 4:
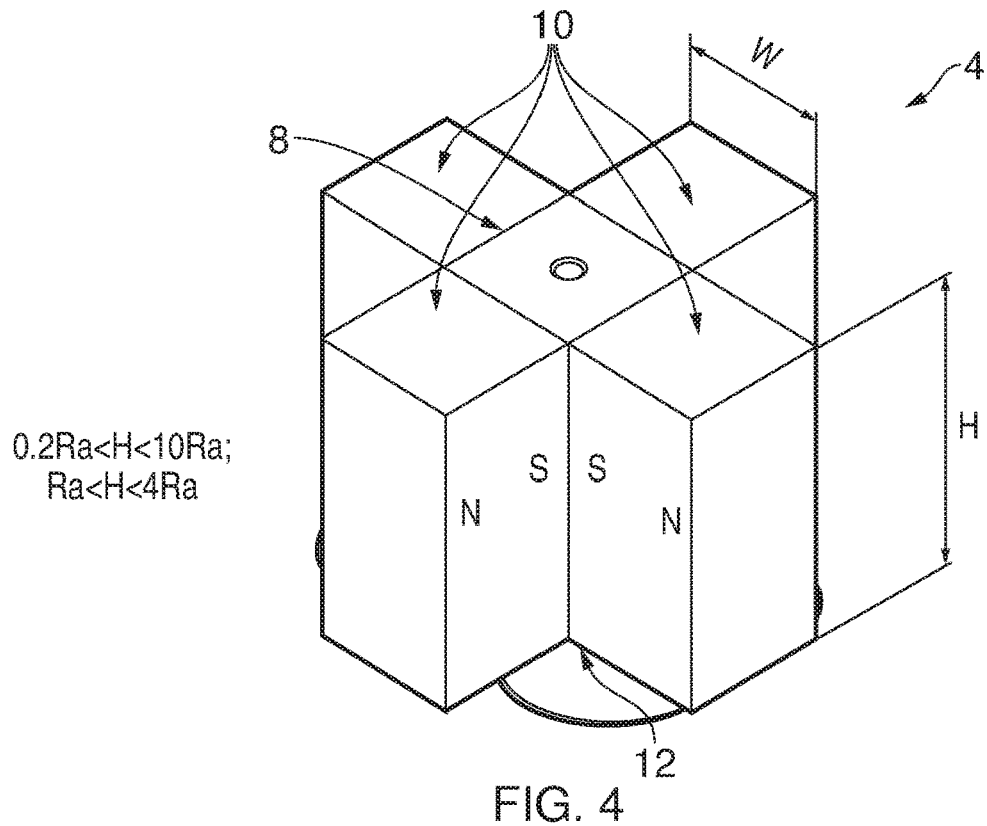
Figure 6A:
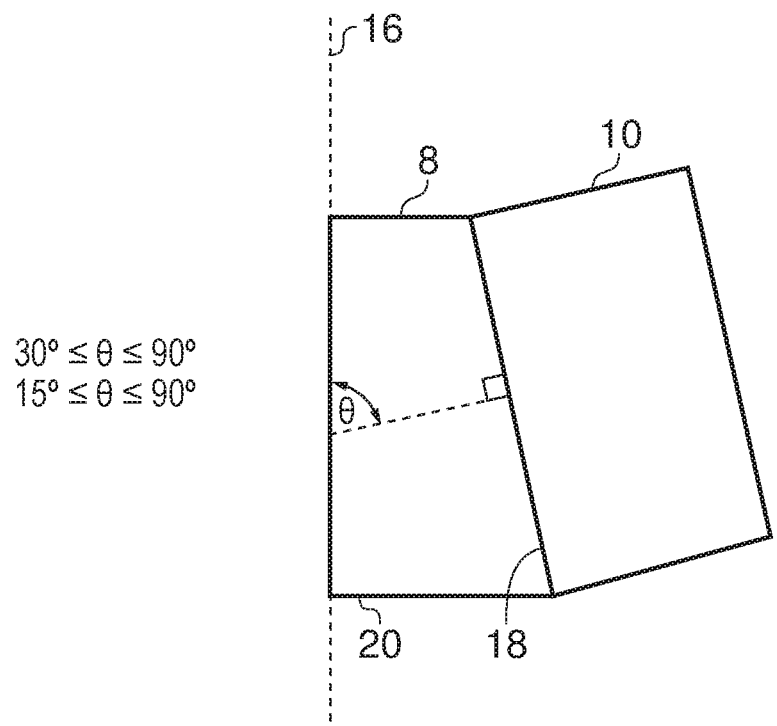
Figure 7:
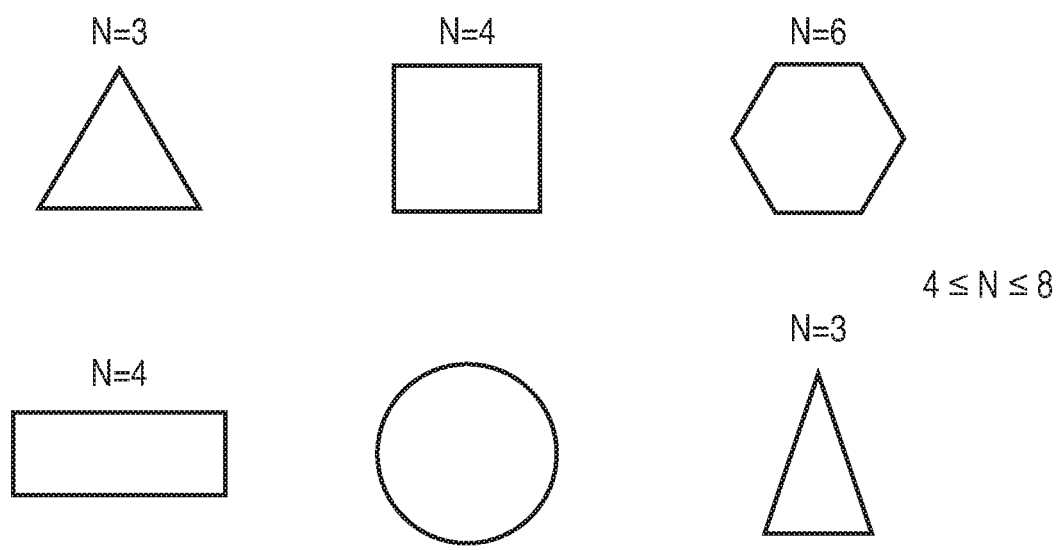
Figure 6B:
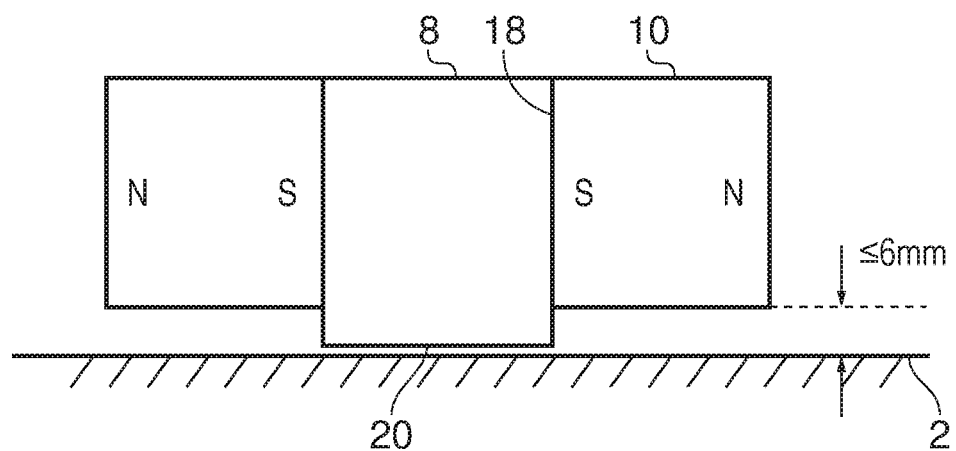
Figure 8A:
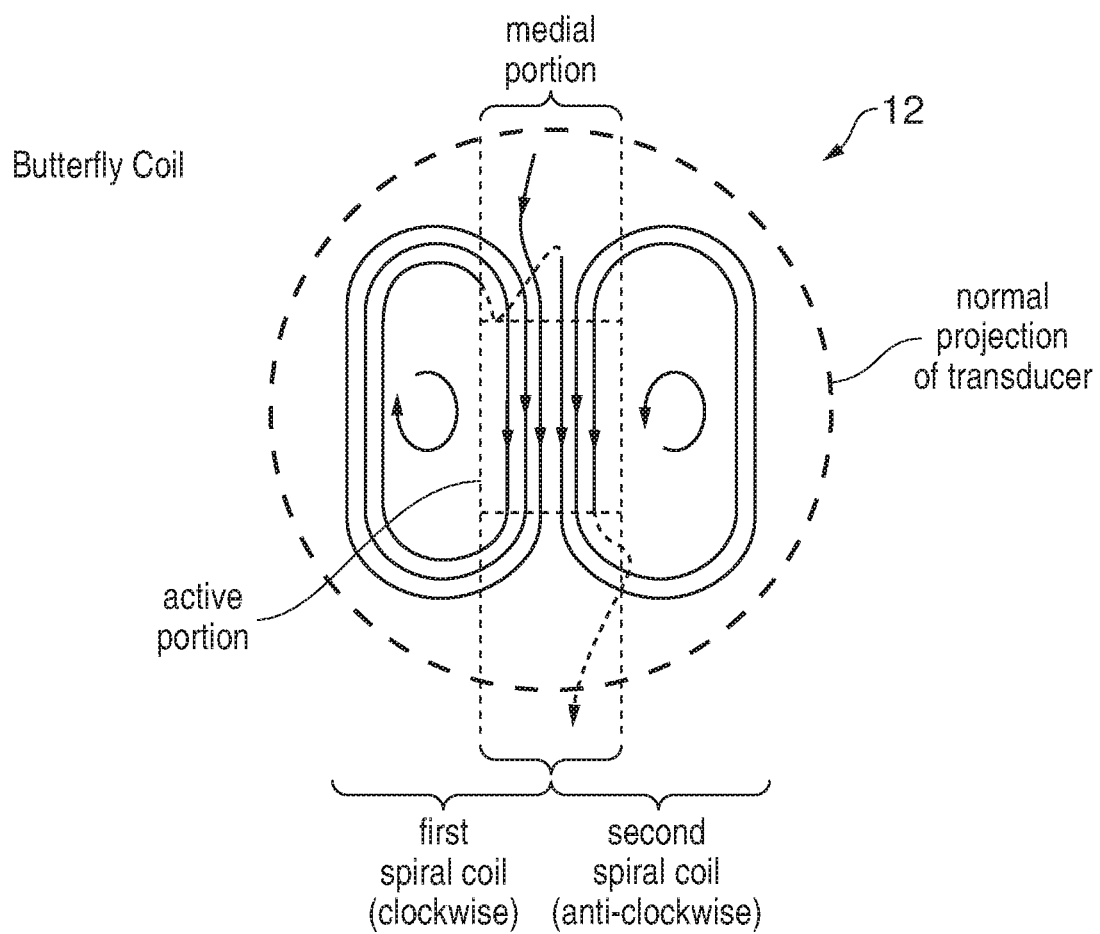
Figure 9:
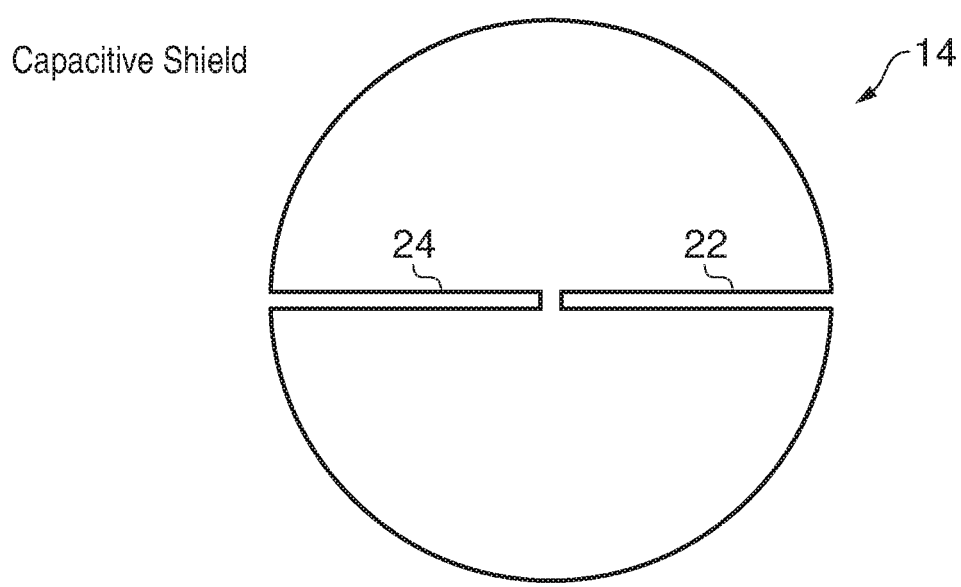
Figure 8B:
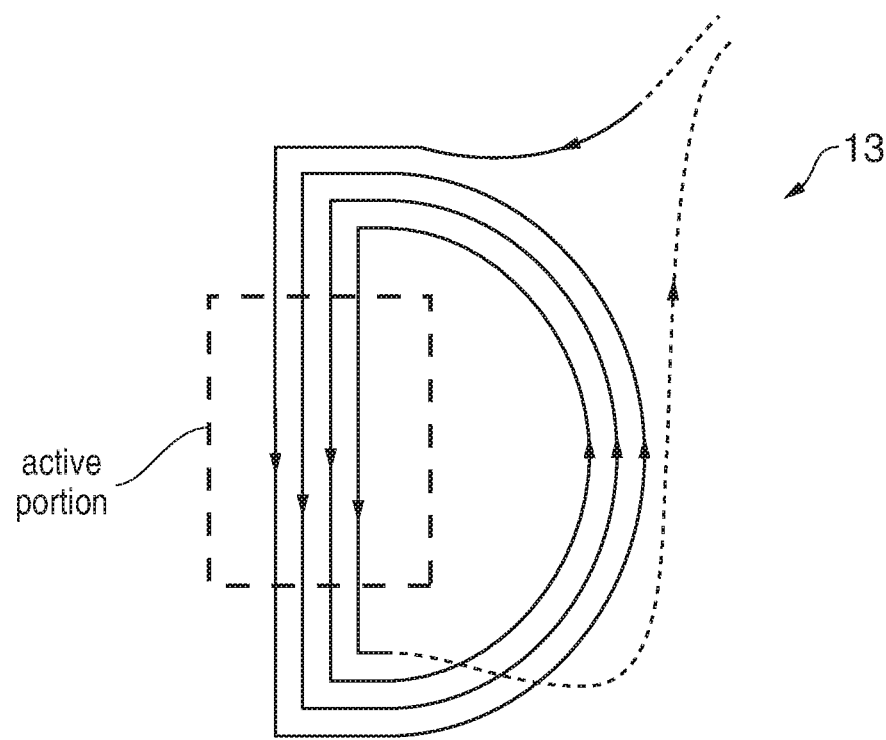
Figure 8C:
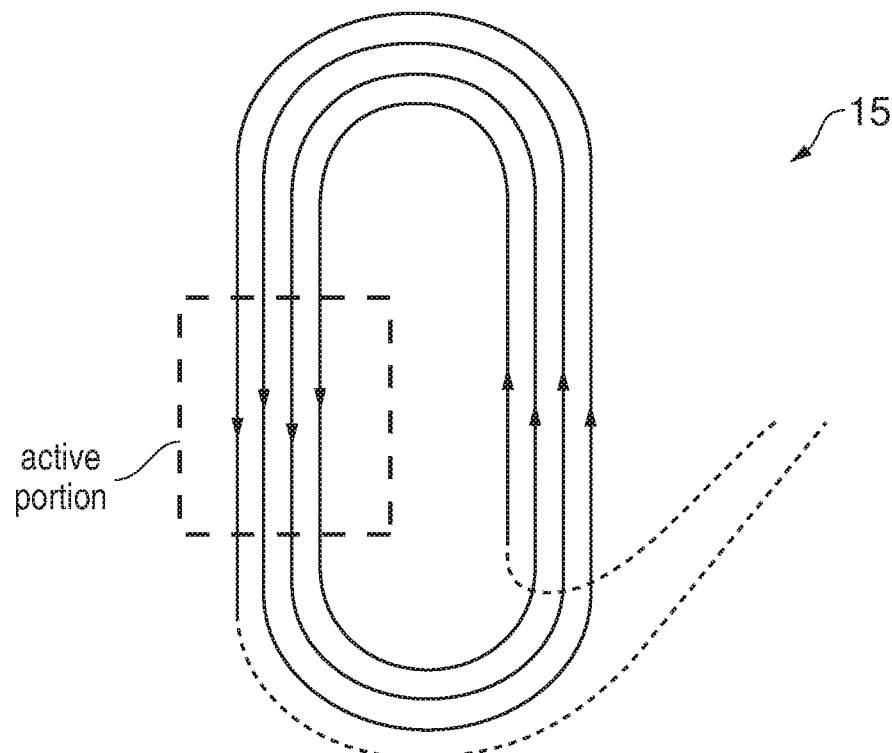
Figure 10:
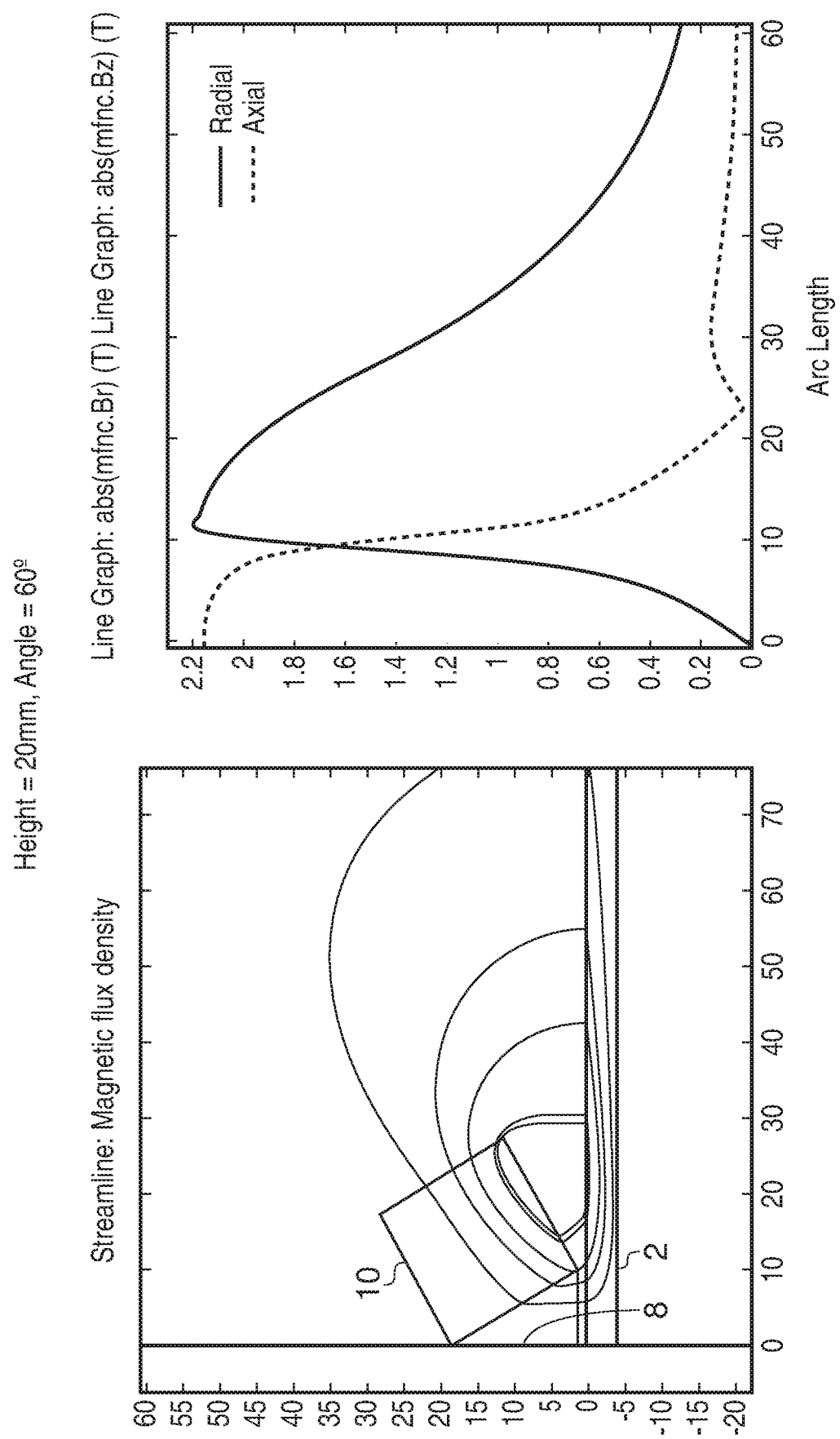
Figure 12:
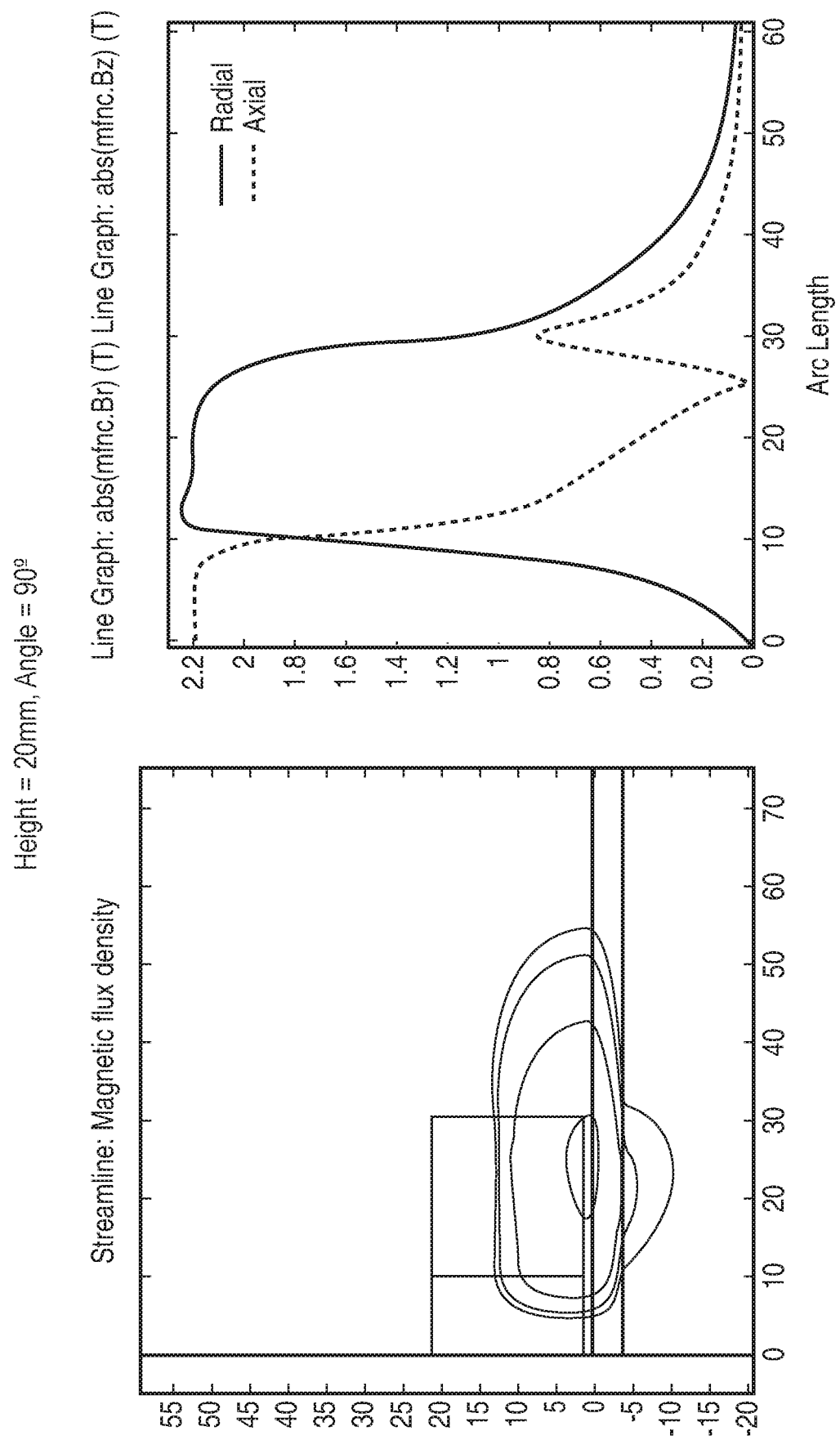
Figure 13:
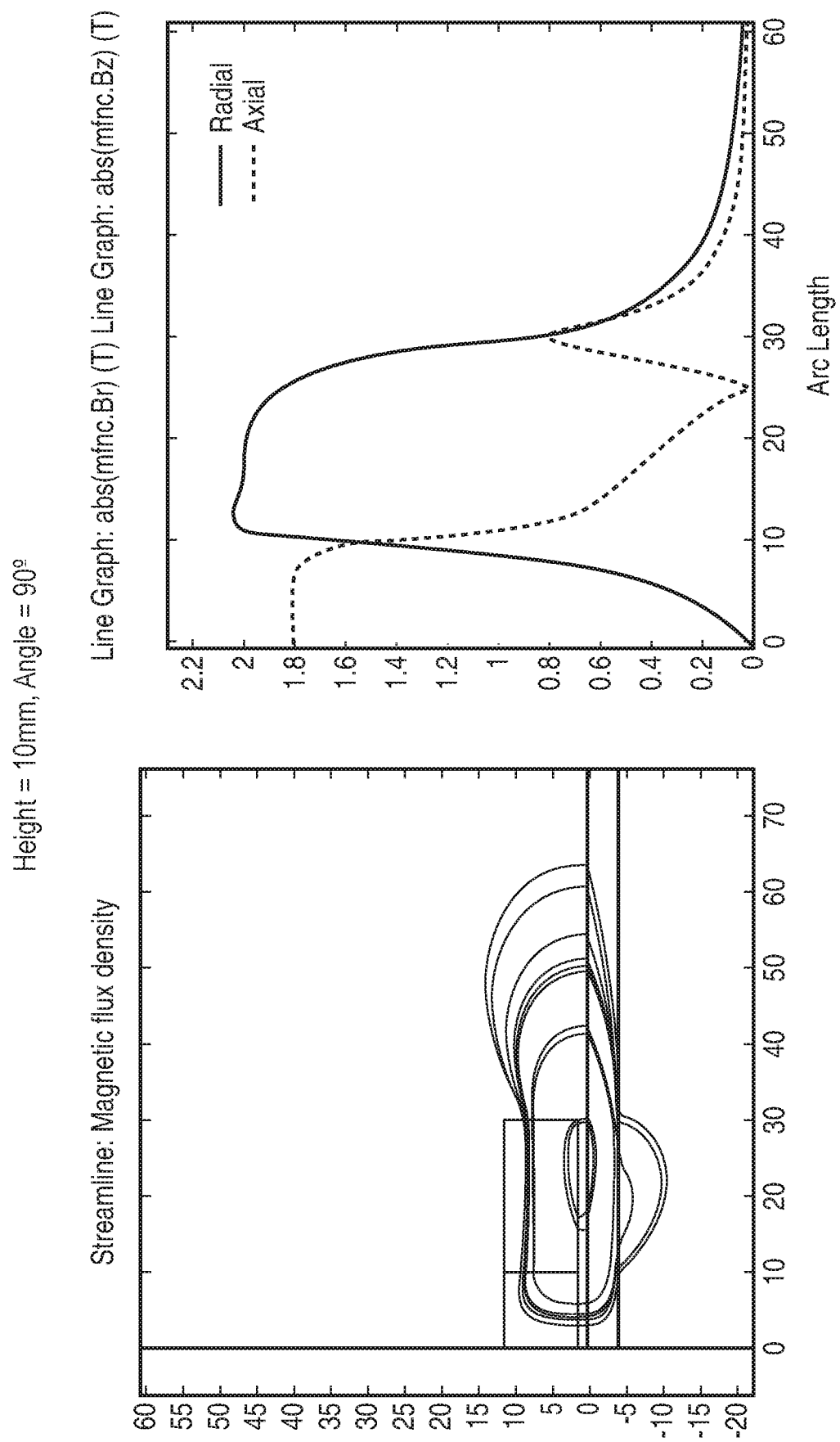
Figure 14:
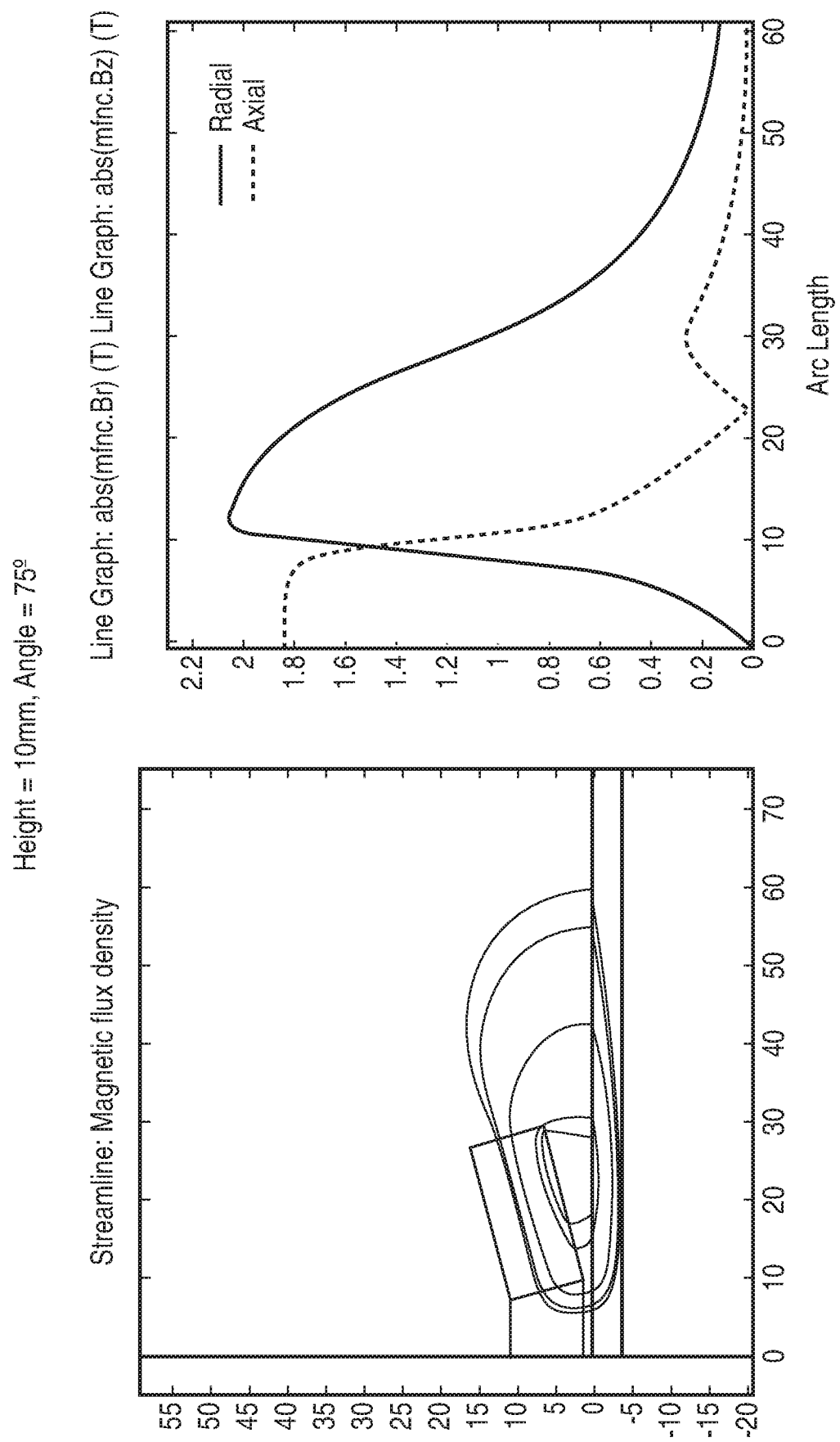
Figure 15:
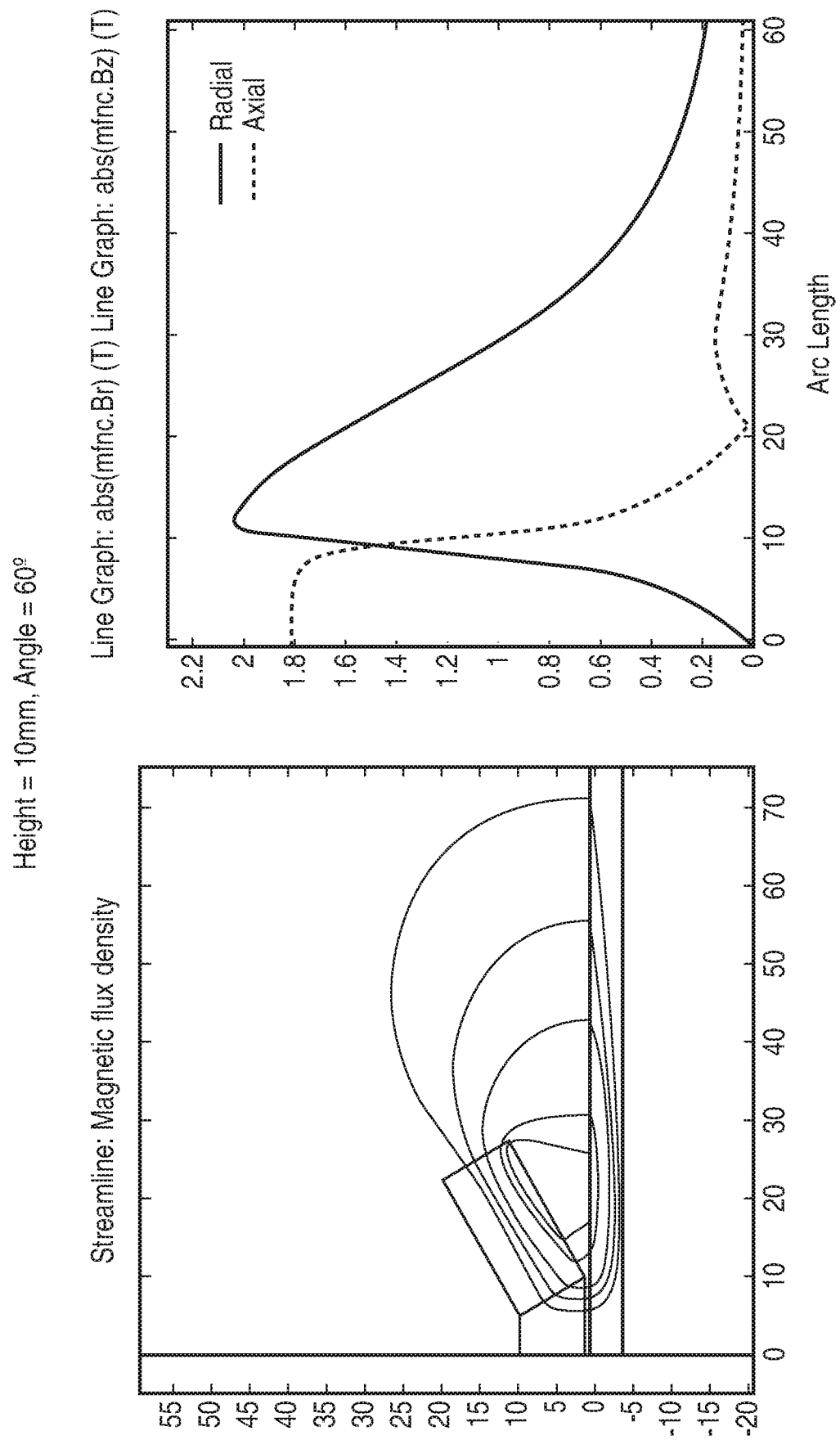
Figure 16:
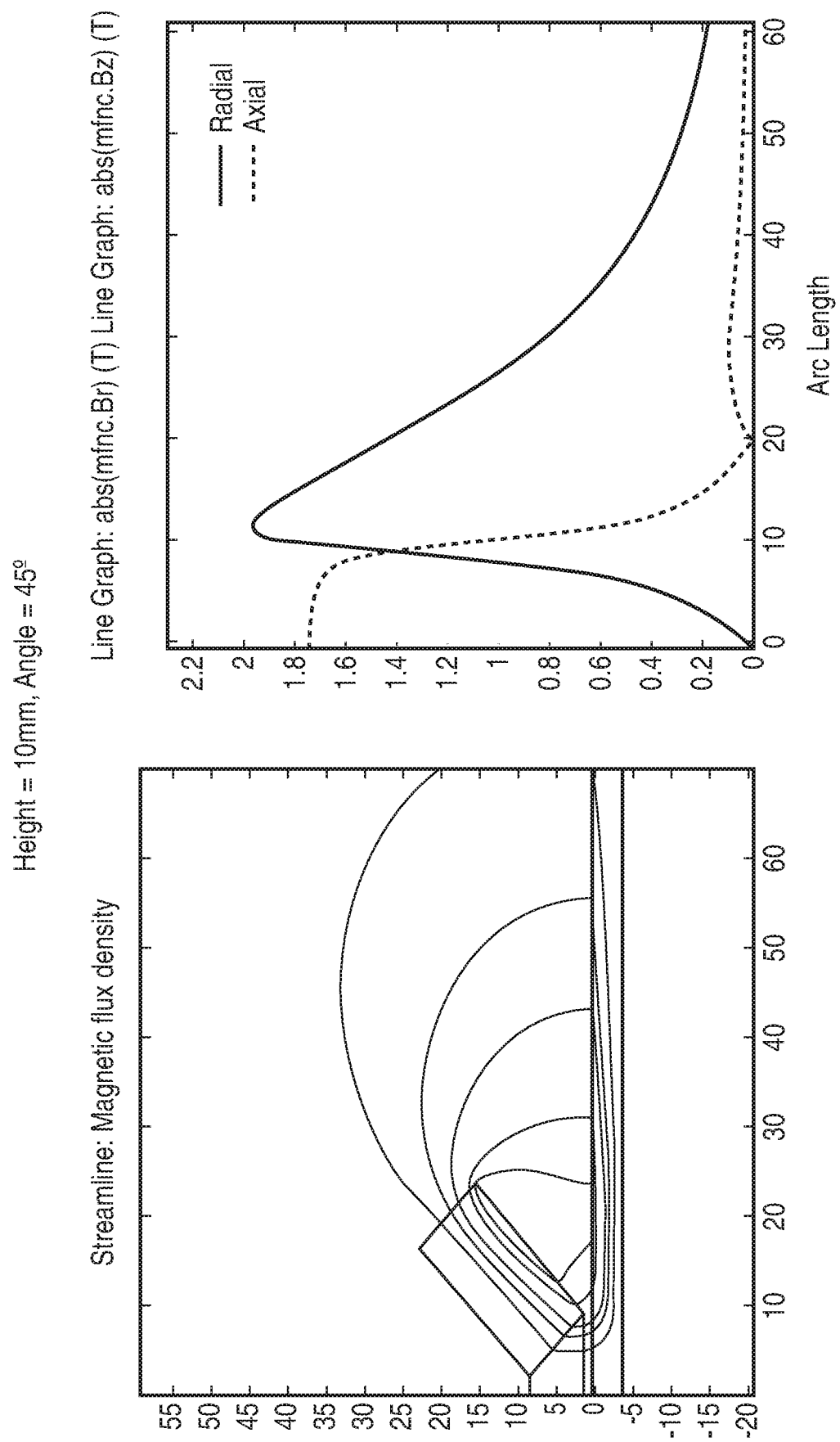
Figure 17:
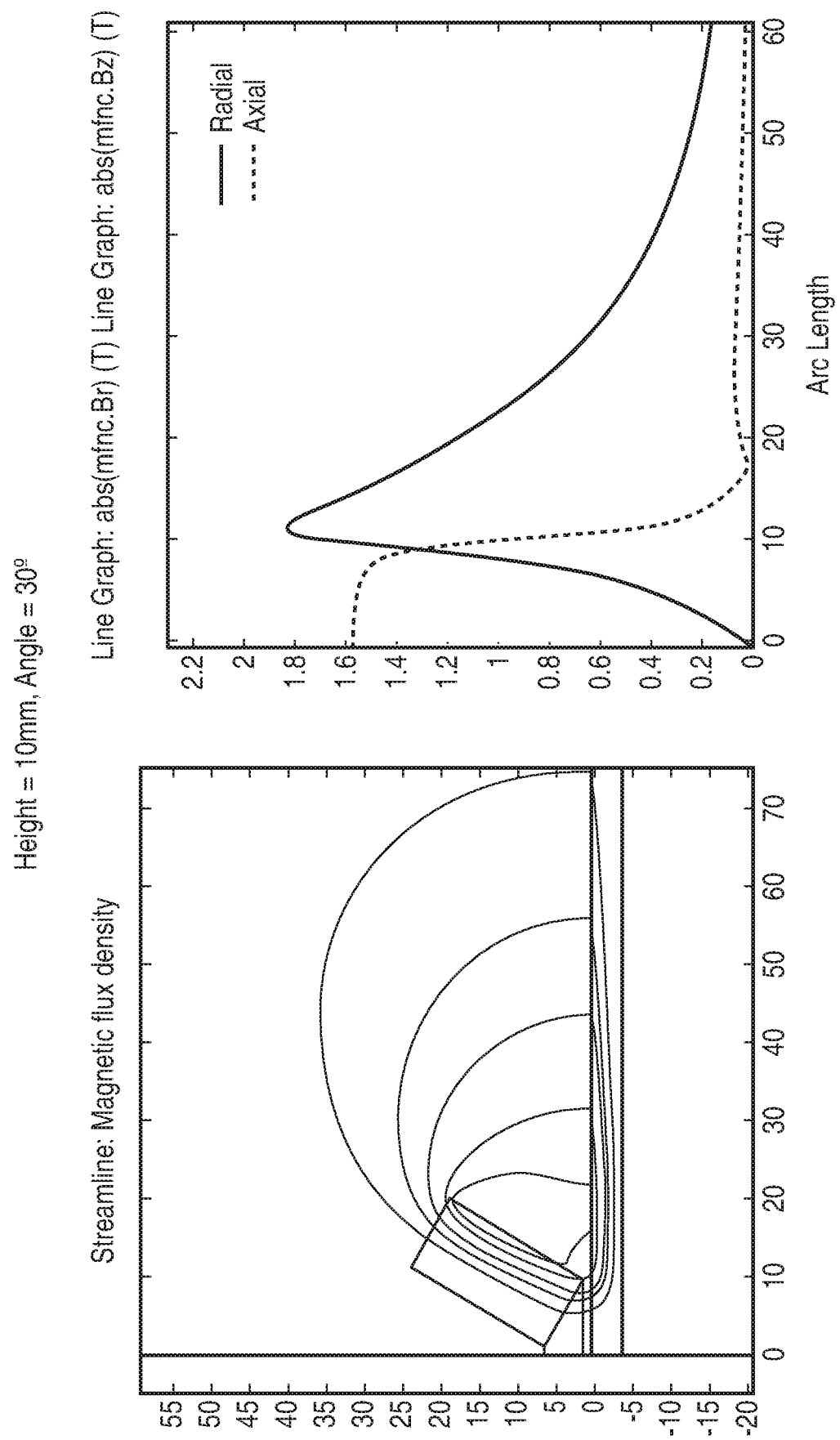
Figure 18:
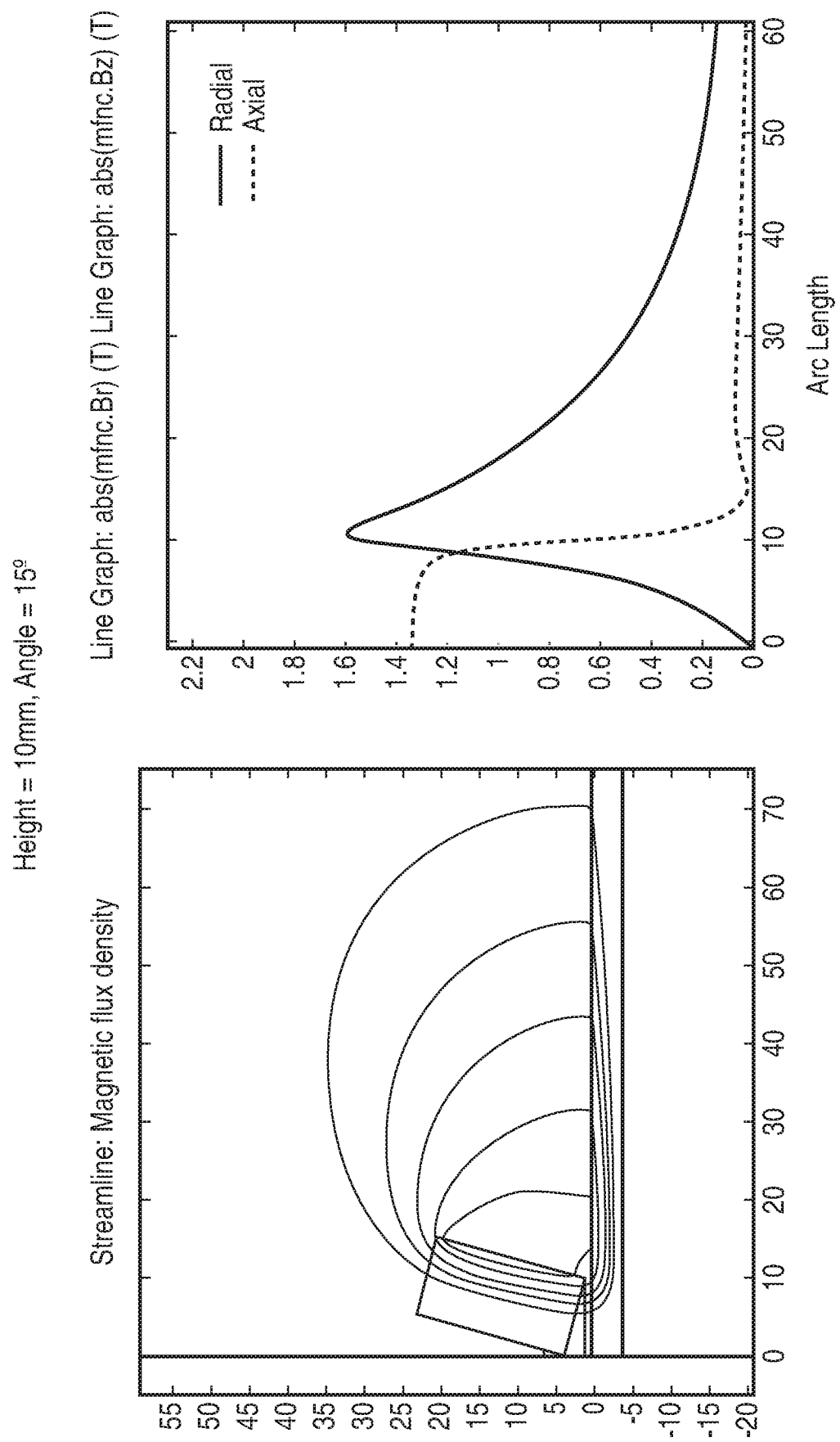
Figure 19:
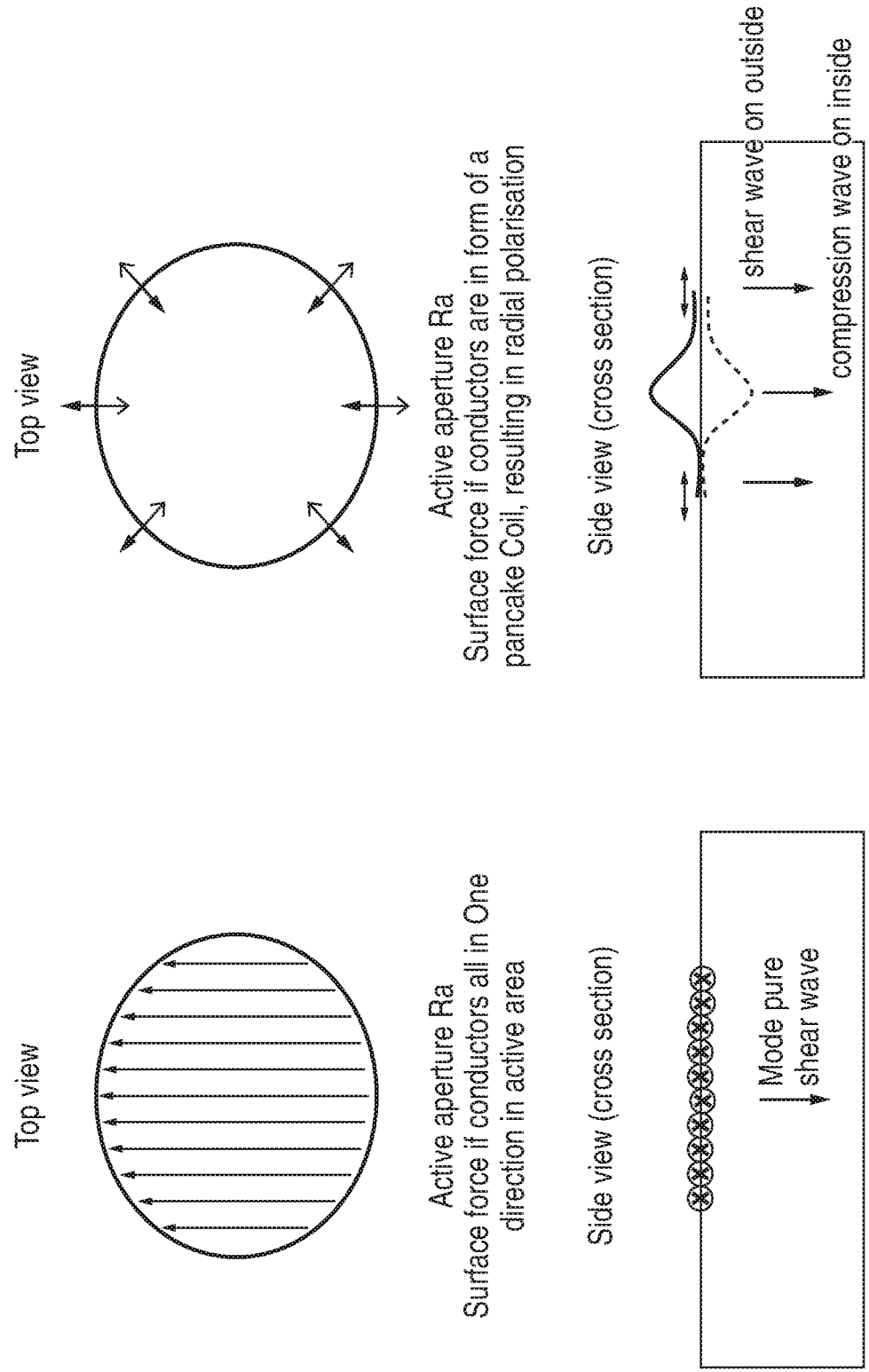
Figure 20:
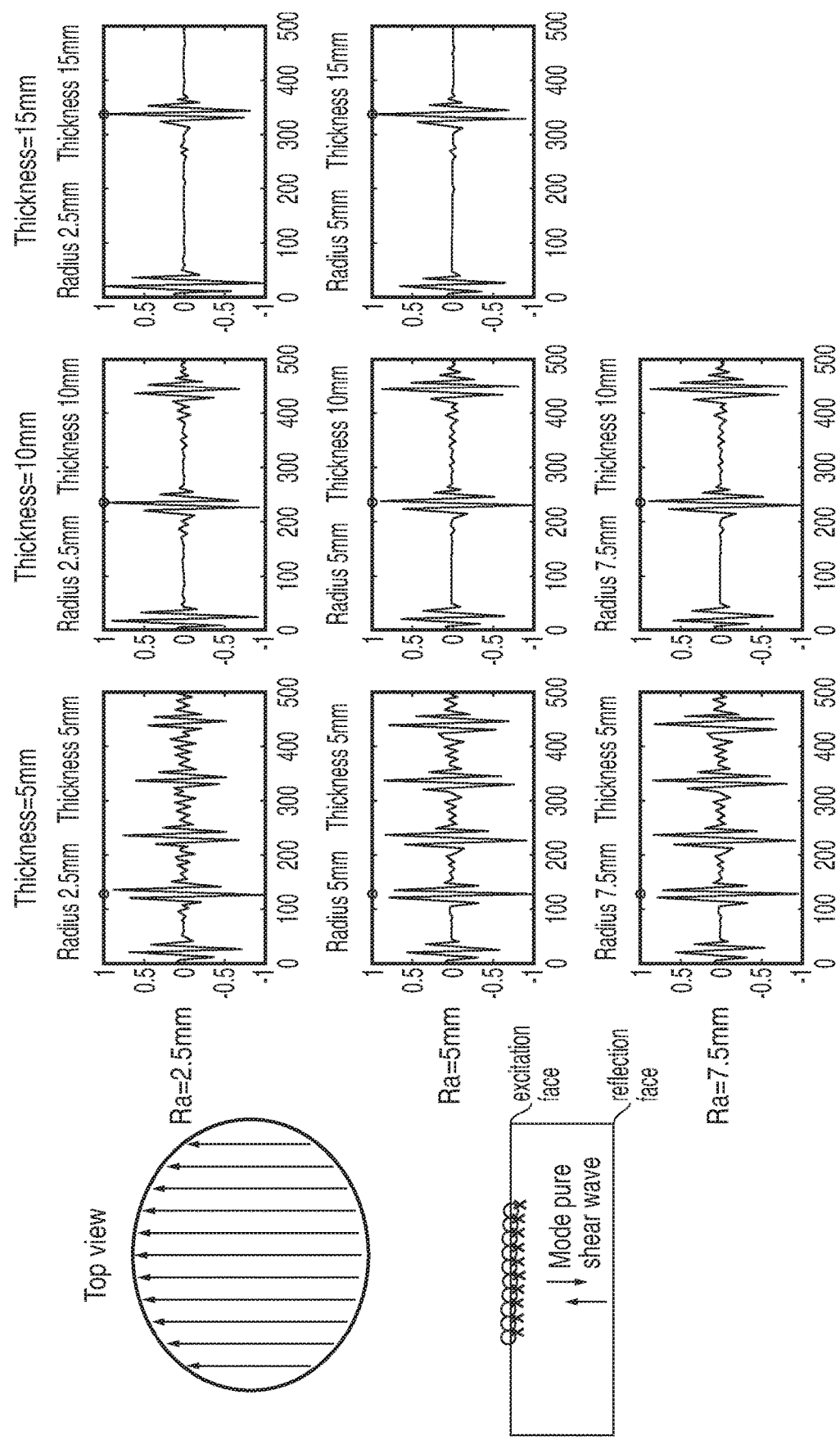
Figure 21:
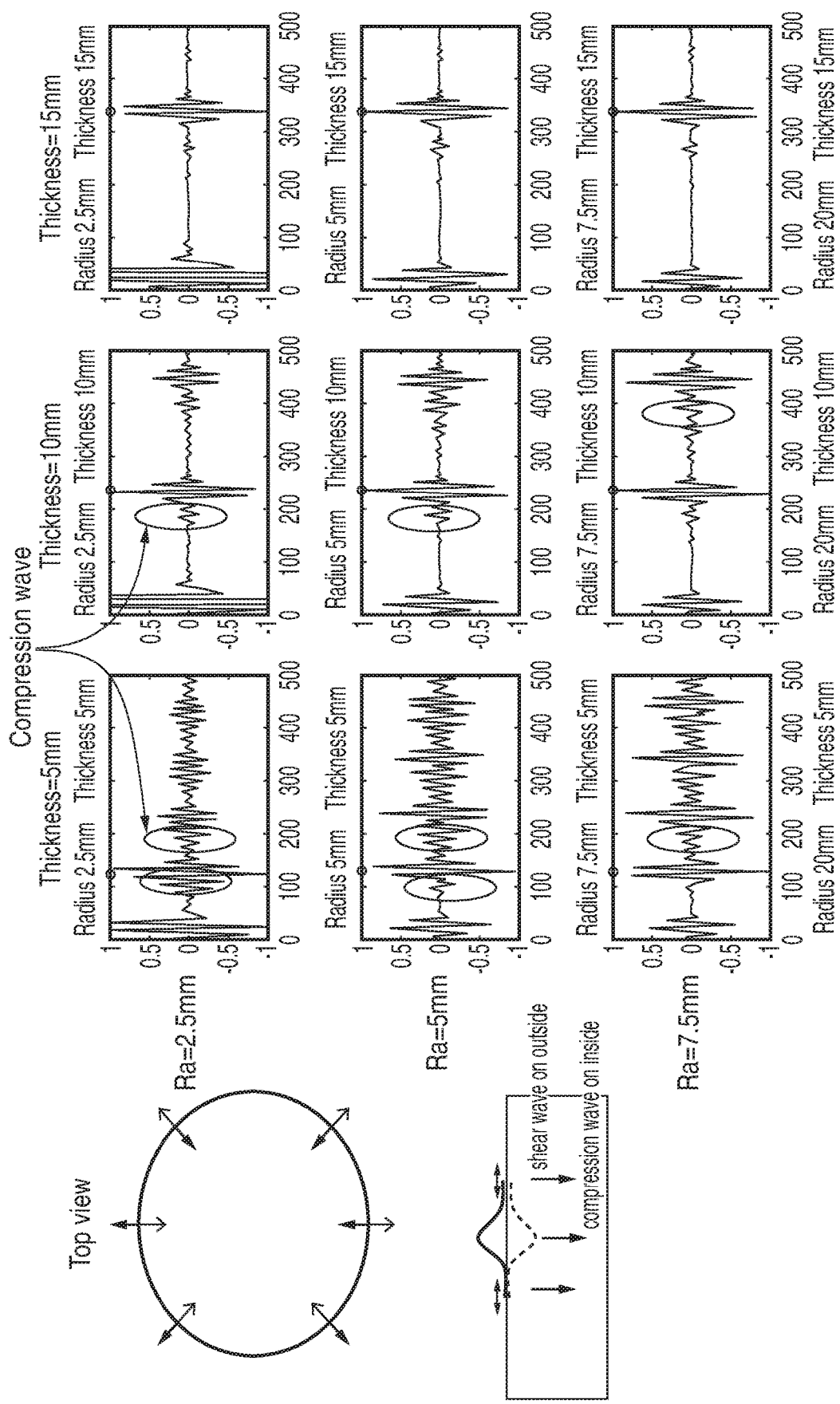

FIG. 4 schematically illustrates a plurality of magnets, a fluxguide and a coil for use in a transducer;

FIG. 5 schematically illustrates magnetic field lines within the transducer of FIG. 2;

FIG. 6A schematically illustrates different angles at which the magnetic field lines may enter the fluxguide relative to the normal to the test face;

FIG. 6B schematically illustrates limiting the distance between the test face of the fluxguide and the contact face between the magnet(s) and the fluxguide;

FIG. 7 schematically illustrates a number of example fluxguide prism or frustum cross-sections;

FIGS. 8A, 8B and 8C schematically illustrates a butterfly coil, a D-shaped coil and a racetrack coil respectively;

FIG. 9 schematically illustrates a capacitive shield for use between a test object and the butterfly coil of FIG. 8;

FIGS. 10 to 18 schematically illustrate the path of magnetic field lines and the magnetic flux density at the test face for fluxguides of a variety of different heights and with the magnetic field passing between the permanent magnet and the fluxguide at a variety of different angles from the normal to the test face; and FIGS. 19, 20 and 21 schematically illustrate different behaviour when exciting mode pure and non-mode pure signals with different forms of coils.

Figure 1:
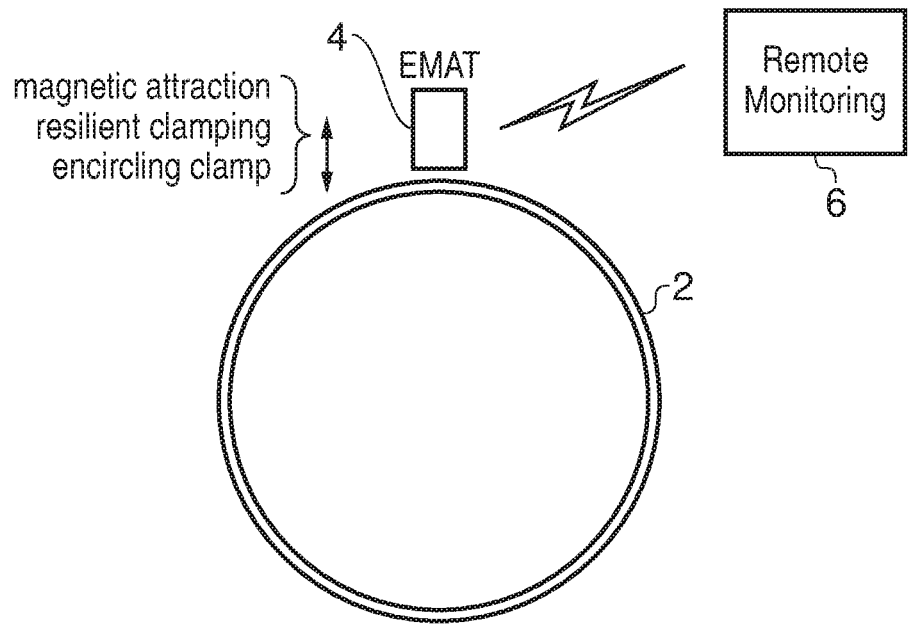

FIG. 1 schematically illustrates an example test object 2, in the form of a steel pipe, which is to be subject to internal corrosion monitoring, defect detection and the like using an electromagnetic acoustic transducer 4 held to the surface of the pipe 2 by one or more of magnetic attraction, resilient clamping to the curved surface of the pipe 2 and/or an encircling clamp passing around the pipe 2. The transducer 4 is battery powered (mains power or energy harvesting may also be used) and is in wireless communication with a remote monitoring system 6, which receives and interprets the results of the ultrasonic tests periodically performed by the transducer 4 upon the pipe 2. The pipe 2 may have an electrically non-conductive coating so as to inhibit external corrosion. For example, the pipe 2 may be painted with such a coating. The electromagnetic acoustic transducer 4 is able to excite and detect ultrasonic signals within the pipe 2 despite this non-conductive coating.

It will be understood that the electromagnetic acoustic transducer 4 is not limited to use in remote monitoring, e.g. it could also be used for standard inspection purposes or other uses.

FIG. 2 is a partially transparent perspective view of the transducer 4. The transducer 4 includes a fluxguide 8 surrounded by a plurality of strong permanent magnets 10. A butterfly coil 12 is disposed between a test face at the base of the fluxguide 8 and the test object 2. A capacitive shield 14 (consisting of a conductive plate with cuts) is disposed between the butterfly coil 12 and the test object. The capacitive shield 14 serves to pass magnetic fields and attenuate electric fields. The capacitive shield 14 also serves as a wear plate to resist damage to the butterfly coil 12. The transducer is contained within a housing 9 that has a magnetic permeability $\mu$ where $\mu$ is less than $2\mu_o$ and $\mu_o$ is the permeability of free space. The housing 9 thus has a low impact upon the magnetic field.

It will be seen from FIG. 2 that the butterfly coil 12 occupies an area which is contained within a total cross-sectional area occupied by the transducer 4 projected normally onto the test object 2. Thus, the electrical coil 12 may be completely contained within the transducer 4 and protected by the transducer body. It is also possible that in other embodiments the electrical coil 12 may extend outside the magnet arrangement and transducer body.

The permanent magnets 10 and the fluxguide 8 in this example embodiment have a height of 40 mm and a width of 20 mm. It will be appreciated that other dimensions may be used and typically the height of the fluxguides and the magnets will be greater than or equal to 0.001 metres and less than or equal to 0.1 metres.

Figure 3:
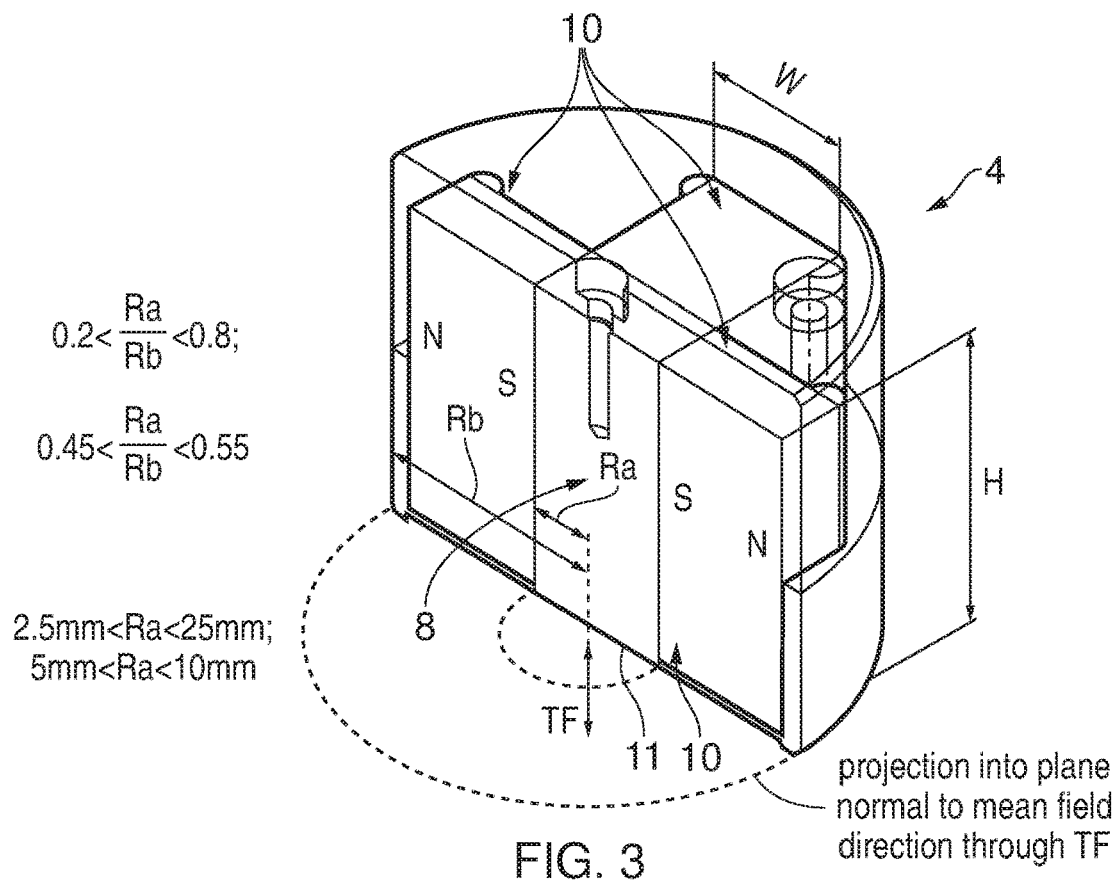
FIG. 3 is a diagram schematically illustrating a cut away view through the transducer of FIG. 2.

FIG. 3 is a partial cut away diagram of the transducer 4 of FIG. 2. As will be seen in FIG. 3, the fluxguide 8 comprises a right prism with a square polygonal face forming the test face 11 which is placed against the test object 2 (although there may be intervening structures, such as the coil 12 and the capacitive shield 14). The test face 11 may in some embodiments be the projection of the flux guide cross-section onto the test object. The permanent magnets 10 have magnet faces which abut the side faces of the fluxguide 8 such that the magnetic field in this example embodiment passes from the permanent magnets 10 into the fluxguide 8 through a face with a normal that is substantially perpendicular to the normal to the test face 11. The majority of magnetic field lines leave the fluxguide 8 through the test face 11 and then enters the test object 2.

The fluxguide 8 has dimensions such that a smallest radius of a circle wholly containing a projection of the test face 11 in a place normal to the mean direction of magnetic field lines passing through the test face is $R_a$ (as shown). $R_a$ may be in the range 2.5 mm to 25 mm or in some embodiments 5 mm to 10 mm. The magnets 10 have dimensions such that a smallest radius of a circle wholly containing a projection of the magnets 10 is $R_b$ and $R_a/R_b$ is in the range 0.2 to 0.8, or in some embodiments in the range 0.45 to 0.55

The fluxguide 8 may be made of a soft magnetic material, such as iron or laminated iron so as to reduce eddy currents on its surface due to the coil. The permanent magnets 10 may be strong magnets that may have magnetic flux densities in excess of 1 Tesla. As will be seen, in this example embodiment, all of the permanent magnets are arranged such that their south poles contact the fluxguide 10. The magnetic field which enters the fluxguide 8 from each of the permanent magnets 10 will accordingly be repelled from the magnetic field(s) entering from the remainder of the magnets 10. This has the effect of directing the magnetic fields towards the test face 11 (or at least part of the magnetic fields) in a manner which results in an increase in the flux density at the test face 11 above that within the permanent magnets 10 alone. In practice, an amplification of the flux density of approximately the order of x3 may be achieved. This improves the sensitivity of the electromagnetic acoustic transducer 4 whose sensitivity may be roughly proportional to the square of the flux density at the test face.

It will be appreciated that the transducer 4 will typically contain many electronic components for driving the coil 12 as well as receiving signals at the coil 12. These electronic components have been omitted from the present figures for the sake of clarity, but can take a substantially conventional form as will be familiar to those in the field of electromagnetic acoustic transducers.

The test face in this example embodiment comprises the square polygonal face at the base of the flux guide 8. A diagonal across this square test face represents the largest dimension of the test face. The present techniques can be used with transducers of a variety of different scales and typically the test face will have a maximum dimension (e.g. diagonal) lying in the range of greater than or equal to 0.001 metres and less than or equal to 0.1 metres. In some embodiments this dimension ($2R_a$) may be in the range 5 mm to 50 mm or the range 10 mm to 20 mm.

FIG. 4 schematically illustrates a perspective view of the permanent magnets 10, the fluxguide 8 and the coil 12 forming part of the transducer 4. As shown in this example, the side faces of the flux guide 10 each abut a south pole of a permanent magnet 10. Repulsion between the magnetic field lines which enter the fluxguide 8 from the permanent magnets 10 serves to direct at least a portion of these magnetic field lines down towards the test face at the end of the flux guide 10 which abuts the test object 2. The butterfly coil 12 is disposed between this test face and the test object 2. The height H of the fluxguide 8 may be in the range $0.2R_a$ to $10R_a$ and in some embodiments in the range $R_a$ to $4R_a$ or in the range 5 mm to 50 mm.

FIG. 5 schematically illustrates a cross-section through the transducer 4 and the test object 2 illustrating the path of magnetic field lines entering the fluxguide 8 from two permanent magnets 10 disposed upon opposite sides of the fluxguide 8. As will be seen, the magnet faces are substantially perpendicular to the normal from the test face at the base of the fluxguide 8. The magnetic field lines entering from opposite sides of the fluxguide 8 repel each other and are directed towards the test face so that they enter the test object 2. The test object 2 provides a return path for the magnetic field guides to their respective magnets 10. The return path through the test object 2 may provide a preferential return path depending upon the magnetic properties of the material from which the test object 2 is formed and the geometry of the test object 2 (e.g. a steel pipe forming the test object 2 may provide a ready return path for the magnetic field lines). The geometry of the transducer 4 is such that a relatively high resistance to lift off of the transducer 4 (magnets) from the surface of the test object 2 is provided. Thus, minor disturbance of the transducer 4 from an ideal contact with the test object 2 does not have an unduly negative effect upon the performance of the transducer 4, e.g. its sensitivity. This makes the performance of the transducer 4 less sensitive to use on curved test objects, e.g. pipes with different/small diameters. This is illustrated in FIG. 6B as discussed below.

FIG. 6A schematically illustrates a cross-section through a fluxguide 8 and a magnet 10 on one side of a central axis 16 of the fluxguide 8. This example illustrates how the side face 18 of the fluxguide 8 against which the magnet face of the magnet 10 is placed may have a normal with an angle to the normal from the test face 20 that lies within a range of angles. As illustrated, acceptable performance may be achieved when the angle lies in the range of greater than or equal to 15 degrees or less than or equal to 90 degrees. Better performance is achieved when this angle is greater than or equal to 30 degrees or less than or equal to 90 degrees. An angle of substantially 90 degrees is convenient for manufacturing and packaging and is in accordance with the example embodiment illustrated in FIGS. 2, 3, 4 and 5.

FIG. 6B schematically illustrates a cross-section through the fluxguide 8 and the magnet(s) 10. In order to reduce susceptibility to "lift off" of the transducer 4 from the test object 2 reducing performance (flux density at the test face 20), the distance between the test face 20 and the contact between the magnet(s) 10 and the fluxguide 8 may be limited to be less than or equal to 6 mm.

It will be appreciated that the fluxguide 8 may have the form of a prism or frustrum. This may, for example, be a right prism. The polygonal face at one end of this right prism or frustrum can have a variety of shapes as illustrated in FIG. 7. These shapes include, for example, an equilateral triangle, a square, a regular hexagon, a rectangle and an isosceles triangle. A limiting case as the number of sides of the polygon forming the end face of the right prism increases is that the end face of the prism will become a circle and the prism will become a cylinder (or in the case of a frustum a conical frustum). In such embodiments, the magnet may take the form of an annular magnet in which the inner face contacting the side face of the cylinder comprises one pole of the magnet with the opposite face of the annulus comprising the other pole of the magnet. Such an annular magnet may, for example, be formed by fixing together a plurality of individually formed and polarised segments of the annulus to form the complete annulus. In some embodiments the test face TF of the fluxguide 8 is a polygon with a number of sides N in the range 4 to 8.

FIG. 8A schematically illustrates an electrical coil in the form of a butterfly coil 12. This butterfly coil 12 comprises two spiral coils wound in opposite senses, i.e. one clockwise and one anti-clockwise when viewed from either above or below. The medial portion of the butterfly coil 12 where the edges of the two spiral coils abut is such that the current through the wires forming the spirals is all passing in the same direction in the medial portion (containing the active portion disposed between the test face and the test object). The wires (conductors) in the medial portion are substantially straight, parallel and passing current in a same direction. This can generate waves of a single polarisation so improving mode purity in the vibrations generated/received (this is discussed further below). This induces a strong eddy current in the test object underlying the medial portion and accordingly, when this interacts with the magnetic field, may be utilised to generate ultrasonic vibrations. As illustrated in FIG. 8A, the butterfly coil 12 is entirely contained within a normal projection of the transducer 4 onto the surface of the test object 2. It will be understood that other forms of electrical coil may also be utilised, such as pancake coils. In some embodiments the butterfly coil 12 may extend outside the normal projection of the transducer 4. The butterfly coil 12 may also be made having a start in the centre of one coil and an end in the centre of the other coil as this avoids crossing the lines in the central region.

FIG. 8B illustrates another example coil in the form of a D-shaped coil 13. This D-shaped coil 13 again has an active portion disposed to cover the test face of the fluxguide 8. The conductors (wires) within the active portion are substantially straight, parallel and carry current in the same direction.

FIG. 8C illustrates another example coil in the form of a racetrack shaped coil 15. This racetrack shaped coil 15 again has an active portion disposed to cover the test face of the fluxguide 8. The conductors (wires) within the active portion are substantially straight, parallel and carry current in the same direction. Small deviations from a straight and parallel arrangement of the various coils 12, 13, 15 are possible while still ensuring that the excited waves are substantially within a single mode.

FIG. 9 schematically illustrates the capacitive shield 14. This takes the form of a conductive plate in which cuts 24 have been made so as to reduce eddy currents induced within the capacitive plates by proximity to the butterfly coil 12. In the drawing only two cuts are shown—more cuts may be used and this may improve performance. The effect of the capacitive shield is that it serves to attenuate (block) electric fields passing between the butterfly coil 12 and the test object 2 whilst permitting magnetic fields to pass between the test object 2 and the butterfly coil 12. The capacitive shield 14 also serves as a wear plate to protect the butterfly coil 12 from physical damage.

FIGS. 10 to 18 schematically illustrate flux lines and radial and axial flux densities within the test object 2 which may be achieved using fluxguides 8 of different heights normal to the surface of the test object 2 and with side faces through which the magnetic field enters the fluxguide 8 that have different angles relative to a normal to the test object 2. The permanent magnet 10 illustrated will in practice be disposed opposite another permanent magnet 10 on the other side of the fluxguide 8, but this is not illustrated in FIGS. 10 to 18. The examples of FIGS. 10 to 18 belong to systems with cylindrical symmetry.

The effect of the two permanent magnets 10 in such close proximity is that the magnet field lines within the fluxguide 8 repel each other and are directed towards the test face of the fluxguide 8 from which they enter the test object 2. The test object 2 may provide a relatively ready return path for these magnetic field lines to the permanent magnet 10 e.g. if the test object 2 is made of a ferromagnetic material. In the example illustrated, the permanent magnet 10 may have a magnetic flux density within its body of less than 1 Tesla whereas it will be seen that the magnet flux densities achieved within the test object 2 may be more than double this level. Even if the test object 2 is not ferromagnetic, an increase in flux density where the magnetic field passes between the fluxguide 8 and the test object 2 may be achieved.

FIGS. 10 to 18 illustrate the magnetic field line paths and the magnetic flux densities achieved for a variety of different heights of the fluxguide 8 together with a variety of different angles at which the permanent magnets 10 abut the fluxguide 8. Acceptable amplification of the magnetic flux density entering the test object 10 may be achieved when the angles lie in the range of 15 degrees to 90 degrees. Better amplification is achieved when the angles are in the range of 30 degrees to 90 degrees. Various heights of fluxguide 8 may be employed as are illustrated.

It will be appreciated that FIGS. 10 to 18 demonstrate that the fluxguide 8 may have a variety of different shapes and forms whilst achieving the effect of utilising repulsion between the magnetic field within the fluxguide 8 to direct that magnetic field towards the test face and the test object such that the magnetic flux density at the test face is greater than that achieved within the permanent magnet 10 alone.

FIG. 19 schematically illustrates an aperture of radius Ra corresponding to an active portion of a coil between a test face and a test object. Within the active portion elastic waves (ultrasonic waves) are excited due the Lorentz force mechanism, which is a result of the interaction of induced eddy currents in the test object (electrically conductive) and the bias magnetic field. When the conductors are substantially parallel across the aperture as shown in the left hand part of FIG. 19, the forces act parallel with single direction resulting in excitation of a mode pure shear wave. In contrast if the coil forms a loop in the active portion as shown in the right hand portion of FIG. 19, then this results in surface forces that radially stretch and radially compress the surface resulting in poorer mode purity, i.e. excitation of longitudinal wave toward a centre portion of the loop.

FIG. 20 schematically illustrates excitation of mode pure signals at 2 MHz at one face (excitation face) of steel plates of respective thicknesses and the received reflected signals (of different orders of reflection) from the opposite face (reflection face). FIG. 21 schematically illustrates excitation of non-mode pure signals at 2 MHz at one face (excitation face) of steel plates of respective thicknesses and the received reflected signals (of different orders of reflection) from the opposite face (reflection face). Comparing the received signals on FIG. 20 to those of FIG. 21, it will be seen that mode pure excited waves result in more clearly separated and more readily discriminated received signals (reflected waves).

Although illustrative embodiments of the invention have been described in detail herein with reference to the accompanying drawings, it is to be understood that the invention is not limited to those precise embodiments, and that various changes, additions and modifications can be effected therein by one skilled in the art without departing from the scope and spirit of the invention as defined by the appended claims. For example, various combinations of the features of the dependent claims could be made with the features of the independent claims without departing from the scope of the present invention.

The invention claimed is:

1. An electromagnetic acoustic transducer for exciting ultrasonic vibrations within a test object, said electromagnetic acoustic transducer comprising:
   at least one magnet configured to generate a magnetic field;
   a fluxguide having a test face for placing against said test object, said fluxguide shaped to receive said magnetic field from said at least one magnet and to direct said magnetic field such that a repulsion between magnetic field lines within said fluxguide directs at least part of said magnetic field towards said test face; and
   an electrical coil comprising conductors, comprising at least:
      an active portion of said electrical coil disposed to cover said test face, wherein within said active portion, said conductors forming the active portion of said electrical coil are substantially parallel, straight and carrying current in a same direction, and
      a further portion of said electrical coil not disposed over said test face, wherein in the further portion, said conductors forming the further portion of said electrical coil carry current in a different direction to the conductors forming the active portion;
   wherein said fluxguide has a shape of a prism or a frustum and said test face is a polygonal base face of said prism or said frustum; and
   a face of said at least one magnet at least partially abuts a side face of the fluxguide; and
   said electromagnetic acoustic transducer comprises a driver component for driving an electrical current through the electrical coil to excite the ultrasonic vibrations within the test object.

2. An electromagnetic acoustic transducer as claimed in claim 1, wherein said electrical coil is a butterfly coil comprising two adjacent spiral coils wound in opposite senses.

3. An electromagnetic acoustic transducer as claimed in claim 2, wherein a medial portion of said butterfly coil between said adjacent spiral coils is said active portion and is disposed between said test face and said test object.

4. An electromagnetic acoustic transducer as claimed in claim 1, wherein
   said test face has dimensions such that a smallest radius of a circle wholly containing a projection of said test face in a plane normal to a mean direction of magnetic field lines passing through said test face is Ra.

5. An electromagnetic acoustic transducer as claimed in claim 4, wherein
   said at least one magnet has dimensions such that a smallest radius of a circle wholly containing a projection of said at least one magnet in said plane is Rb; and
   Ra/Rb is in the range 0.2 to 0.8.

6. An electromagnetic acoustic transducer as claimed in claim 5, wherein Ra/Rb is in a range 0.45 to 0.55.

7. An electromagnetic acoustic transducer as claimed in claim 4, wherein Ra is in a range 2.5 mm to 25 mm.

8. An electromagnetic acoustic transducer as claimed in claim 7, wherein Ra is in the range 5 mm to 10 mm.

9. An electromagnetic acoustic transducer as claimed in claim 4, wherein said fluxguide has a height normal to said plane of H and H is in a range of one of; 0.2Ra to 10Ra; and Ra to 4Ra.

10. An electromagnetic acoustic transducer as claimed in claim 9, wherein 1H is in the range 5 mm to 50 mm.

11. An electromagnetic acoustic transducer as claimed in claim 1, wherein said at least one magnet has one or more magnet faces proximal to said fluxguide and said magnetic field passes between said one or more magnet faces and said fluxguide in respective directions that are non-normal to said test face.

12. An electromagnetic acoustic transducer as claimed in claim 1, wherein said repulsion of said magnetic field lines increases a flux density within said fluxguide and said test face above that within said at least one magnet.

13. An electromagnetic acoustic transducer as claimed in claim 12, wherein the flux density within said fluxguide and said test face is more than double a flux density within said at least one magnet.

14. An electromagnetic acoustic transducer as claimed in claim 1, wherein said polygonal base face is an N sided polygon, where N is in a range 4 to 8.

15. An electromagnetic acoustic transducer as claimed in claim 1, comprising a housing surrounding said at least one magnet and said fluxguide, said housing having a magnetic permeability μ, where μ is less than 2 μo and μo is a permeability of free space.

16. A method of exciting ultrasonic vibrations within a test object using an electromagnetic acoustic transducer, said method comprising the steps of:
- placing a fluxguide with a test face against said test object;
- generating a magnetic field with at least one magnet;
- receiving in said fluxguide said magnetic field from said at least one magnet; directing said magnetic field within said fluxguide such that a repulsion between magnetic field lines directs at least part of said magnetic field towards said test face;
- providing at least an active portion of an electrical coil disposed to cover said test face and a further portion of said electrical coil not disposed over said test face, the electrical coil comprising conductors, wherein within said active portion, said conductors of said electrical coil are substantially parallel, straight and carrying current in a same direction, and in the further portion, said conductors of said electrical coil carry current in a different direction to the conductors in the active portion; and
- driving an electric current through said coil to excite substantially mode pure and uni-directionally polarised shear wave in said test object;
- wherein said fluxguide has a shape of a prism or a frustum and said test face is a polygonal base face of said prism or said frustum; and
- a face of said at least one magnet at least partially abuts a side face of the fluxguide.

* * * * *